(12) United States Patent
Vyas et al.

(10) Patent No.: US 11,014,907 B2
(45) Date of Patent: May 25, 2021

(54) OCTENDIDINE BASED COMPOUNDS

(71) Applicant: DISHMAN CARBOGEN AMCIS LTD., Ahmedabad (IN)

(72) Inventors: Janmejay Rajnikant Vyas, Ahmedabad (IN); Nilesh D. Patel, Ahmedabad (IN)

(73) Assignee: Dishman Carbogen Amcis Ltd., Ahmedabad (IN)

( * ) Notice: Subject to any disclaimer, the term of this patent is extended or adjusted under 35 U.S.C. 154(b) by 0 days.

(21) Appl. No.: 16/640,418

(22) PCT Filed: Aug. 21, 2018

(86) PCT No.: PCT/IB2018/056310
§ 371 (c)(1),
(2) Date: Feb. 20, 2020

(87) PCT Pub. No.: WO2019/038669
PCT Pub. Date: Feb. 28, 2019

(65) Prior Publication Data
US 2020/0377471 A1 Dec. 3, 2020

(30) Foreign Application Priority Data
Aug. 21, 2017 (IN) .............................. 201721029564

(51) Int. Cl.
*C07D 401/06* (2006.01)
(52) U.S. Cl.
CPC ........ *C07D 401/06* (2013.01); *C07B 2200/13* (2013.01)

(58) Field of Classification Search
None
See application file for complete search history.

(56) References Cited

U.S. PATENT DOCUMENTS

| 2008/0103526 A1 | 5/2008 | Vogt et al. |
| 2015/0328115 A1 | 11/2015 | Gruber et al. |
| 2015/0335757 A1 | 11/2015 | Behrends et al. |

FOREIGN PATENT DOCUMENTS

| EP | 1123927 A1 * | 8/2001 | .............. A61P 31/00 |
| EP | 2113237 | 11/2009 | |
| RU | 2323928 C | 5/2008 | |

OTHER PUBLICATIONS

PCT International Search Report dated Jan. 8, 2019, Application No. PCT/IB2018/056310.
PCT Written Opinion dated Jan. 8, 2019, Application No. PCT/IB2018/056310.

* cited by examiner

*Primary Examiner* — Zinna Northington Davis
(74) *Attorney, Agent, or Firm* — The Dobrusin Law Firm, PC

(57) ABSTRACT

The present invention discloses Octenidine based compounds of formula (A) or formula (B) and formula (C) where in, n=1, 2, 3, 4 and R'=un-substituted or substituted aryl or alkyl group; R is hydroxy or hydrogen, X is chlorine, bromine and iodine. The present invention also relates to a process for the preparation thereof.

20 Claims, 32 Drawing Sheets

OCTENDIDINE BASED COMPOUNDS

FIELD OF THE INVENTION

Figure 1:
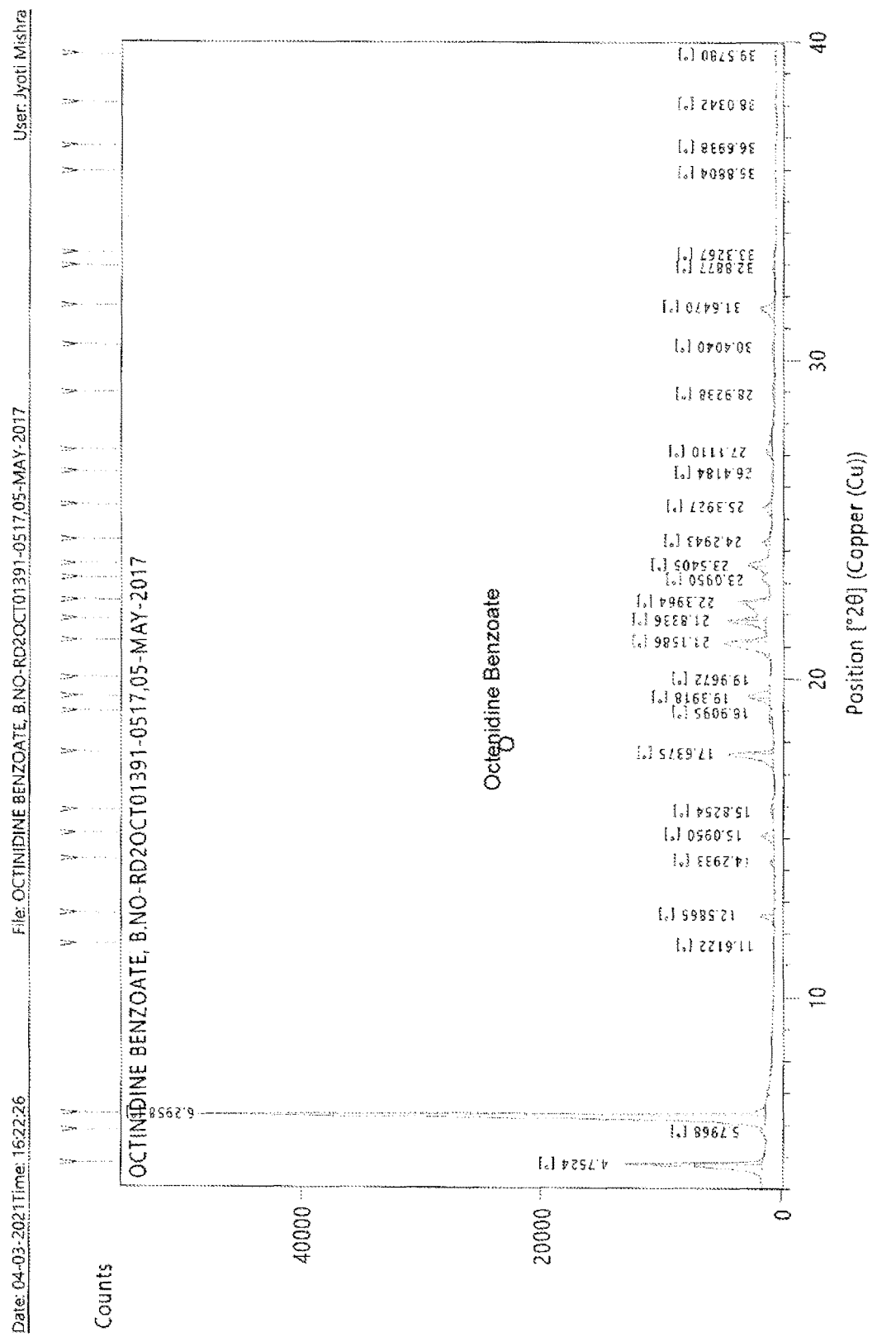

The present invention relates to Octenidine based compounds, particularly polymorphic forms of Octenidine salts. The present invention further relates to the process for the preparation of Octenidine based compounds.

BACKGROUND OF THE INVENTION

Octenidine dihydrochloride is chemically known as N,N'-(1,1'-(decane-1,10-diyl)bis(pyridin-1(1H)-yl-4(1H)-ylidene))dioctan-1-amine dihydrochloride, as represented in Formula

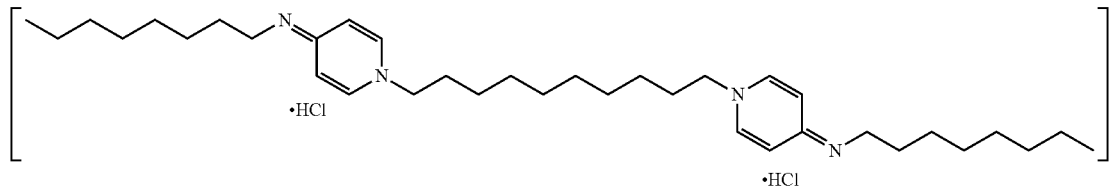

Octenidine dihydrochloride (N,N'-(1,10-Decandiyldi-1(4-H)-pyridynyl-4yliden)bis(1-octan amine)-dihydrochloride-CAS No. 70775-75-6) has been found to be effective disinfectant in various applications. Octenidine dihydrochloride has been used as an antiseptic agent in human medicine.

U.S. Pat. No. 3,055,902 discloses the preparation Octenidine dibromide converted to free base of the Octenidine then converted to tetra hydochloride, in general statement given in description "Salts of the compounds of this invention are particularly therapeutically acceptable acid addition salts with inorganic acids, such as mineral acids, e.g. hydrochloric, hydrobromic, sulfuric or phosphoric acids and the like, with organic carboxylic acids, e.g. formic, acetic, pro-, pionic, glycolic, lactic, pyruvic, malonic, suocinic, maleic, hydroxymaleic, dihydydromaleic, fumaric, malic, tartaric, citric, benzoic, cinnamic, mandelic, salicyclic, 4-a-minosalicylic, Z-phenoxybenzoic or 2-acetoxybenzoic, and the like, or with organic sulfonic acids, e.g. methane sulfonic, ethane sulfonic or 2-hydroxyethane sulfonic acids. Salts, which are primarily used for identification purposes, are particularly those with acidic organic nitro compounds, e.g. picric, picrolonic or flavianic acid, or with metal complex acids, e.g. phosphotungstic, phosphomolybdic, chloroplatinic or Reinecke acid. Mono-, more particularly poly-, such as bisor tetra-salts may be formed, depending on the procedure used for the preparation of the salts and/or the number of salt-forming groups present". However, no preparation of acid additional salts and no characterization data have been provided.

U.S. Pat. No. 4,206,215 discloses the preparation of Octenidine dihydrochloride in inert solvents, such as a lower alkanol, acetonitrile, N,N-dimethylformamide, N,N-dimethylacetamide, benzene, toluene or xylene at a temperature from 80 to 150° C. for a period of from 1 to 24 hours, and also the reaction in the absence of a solvent by heating stoichiometric amounts of the reaction components for from about 2 to 5 hours at 120 to 150° C. Aprotic solvents and similar reaction conditions are described by Bailey et al. in J. Med. Chem. 1984, 27, 1457-64.

U.S. Pat. No. 4,598,082 discloses the preparation of Octenidine dihydrochloride and Octenidine mono saccharine salt.

U.S. Pat. No. 6,380,391 discloses the preparation of Octenidine dihydrochloride in solvents and water.

Accordingly, the object of the present invention was to develop a simple process for the preparation of Octenidine dihydrochloride which does not have the above-mentioned disadvantages. This preparation process should be advantageous particularly from a production efficiency viewpoint. Because Octenidine dihydrochloride, inter alia, is used in pharmaceutical and body hygiene products etc., and the corresponding specifications have to be satisfied, it must also be free from traces of any toxicologically unacceptable impurity, which can originate, for example, from the solvent used.

Further, the prior art processes involve the use of expensive reagents, additional purifications and laborious process for the preparation of Octenidine dihydrochloride. Hence, there is a need in the art to develop an improved process for the preparation of Octenidine based compounds.

US2009/297458 Production of Octenidine Dilactate, octenidine dihydrochloride, stirring is carried out for 10 mins and a stoichiometric quantity of silver lactate is added.

The present inventors have now found an improved process for the preparation of Octenidine based compounds, which is simple, industrially applicable and yields Octenidine based compounds in high purity.

Objective of the Invention

The object of the present invention is to provide novel form of the Octenidine based a compounds.

The object of the present invention is to provide novel crystalline form of the Octenidine acid addition salts.

Yet another object of the present invention is to provide a process for the preparation of novel crystalline form of the Octenidine based compounds.

SUMMARY OF THE INVENTION

The object of the present invention is to provide novel forms of the Octenidine as represented by Formula (A), Formula (B) and Formula (C).

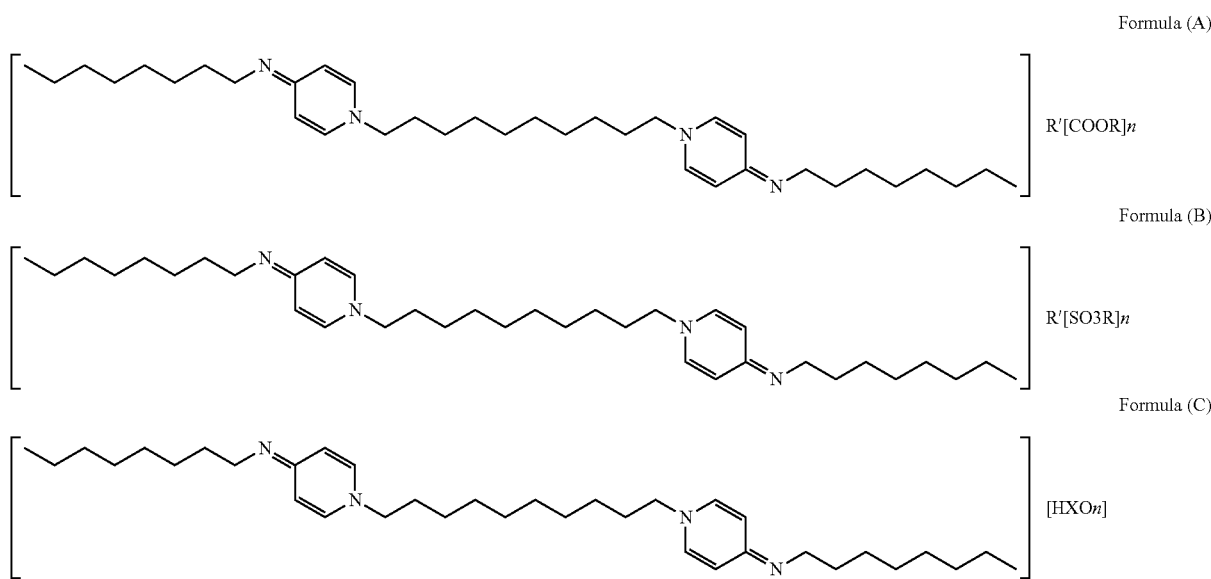

Formula (A)

Formula (B)

Formula (C)

where in, n=1, 2, 3, 4 and R'=un-substituted or substituted aryl or alkyl group; R is hydroxy or hydrogen, X is chlorine, bromine and iodine.

wherein, n=1 and R'=un-substituted or substituted aryl or alkyl group; and n=2 and R'=un-substituted or substituted alkyl or aryl group.

wherein, n=1 and R'=un-substituted or substituted aryl or alkyl group; i.e. benzoic acid, salicylic acid, p-methyl benzoic acid, acetate, peracetic acid, laureate, palmitate etc. and n=2 and R'=un-substituted or substituted alkyl or aryl group. i.e. oxalic acid, malonic acid, succinic acid, tartaric acid, gluconate etc.

wherein, n=1 and R'=un-substituted or substituted aryl or alkyl group; R═H; i.e. methane sulfonic acid, ethane sulfonic acid, propane sulfonic acid, benzene sulfonic acid, p-toluene sulfonic acid etc.

wherein, n=1, 2, 3, 4, hypohalous acid (HXO), halous acid ($HXO_2$) halic acid ($HXO_3$) and perhalic acid ($HXO_4$) n=4 and X═Cl, Br, I, i.e. HClO, $HClO_2$, $HClO_3$, $HClO_4$, HBrO, $HBrO_3$, $HBrO_4$, HIO, $HIO_3$, $HIO_4$.

The present invention provides a process of preparation of crystalline Octenidine based compounds of formula (A), which comprises of:
(a) treating with Octenidine with suitable organic acid in a solvent;
(b) isolating the product as a salt with organic acid from an organic solvent; optionally stage (c)
(c) purifying the salt from organic solvent.

Organic acid may be selected from oxalic acid, malonic acid, succinic acid, tartaric acid, gluconate, laureate, palmitate etc.

The present invention further provides a process of preparation of crystalline Octenidine based compounds of formula (B), which comprises of:
(a) treating with Octenidine with sulfonic acid in a solvent;
(b) isolating the product as a salt with organic acid from an organic solvent; optionally stage (c)
(c) purifying the salt from organic solvent.

Sulfonic acid may be selected from methane sulfonic acid, ethane sulfonic acid, propane sulfonic acid, benzene sulfonic acid, p-toluene sulfonic acid.

The present invention further provides a process of preparation of crystalline Octenidine based compounds of formula (C), which comprises of:
(a) treating with Octenidine with per halogenate acid in a solvent;
(b) isolating the product as a salt with organic acid from an organic solvent;
(c) purifying the salt from organic solvent.

Per halogenate acid may be selected from HClO, $HClO_2$, $HClO_3$, $HClO_4$, HBrO, $HBrO_3$, $HBrO_4$, HIO, $HIO_3$, $HIO_4$.

The present invention further provides a crystalline form of Octenidine benzoate, acetate, gluconate, peracetate, perchloroacetate, laureate, palmitate, methane sulfonic acid.

BRIEF DESCRIPTION OF THE ACCOMPANYING DRAWINGS

FIG. 1. The crystalline form of Octenidine benzoate salt having X-ray powder diffraction pattern.

Figure 2:
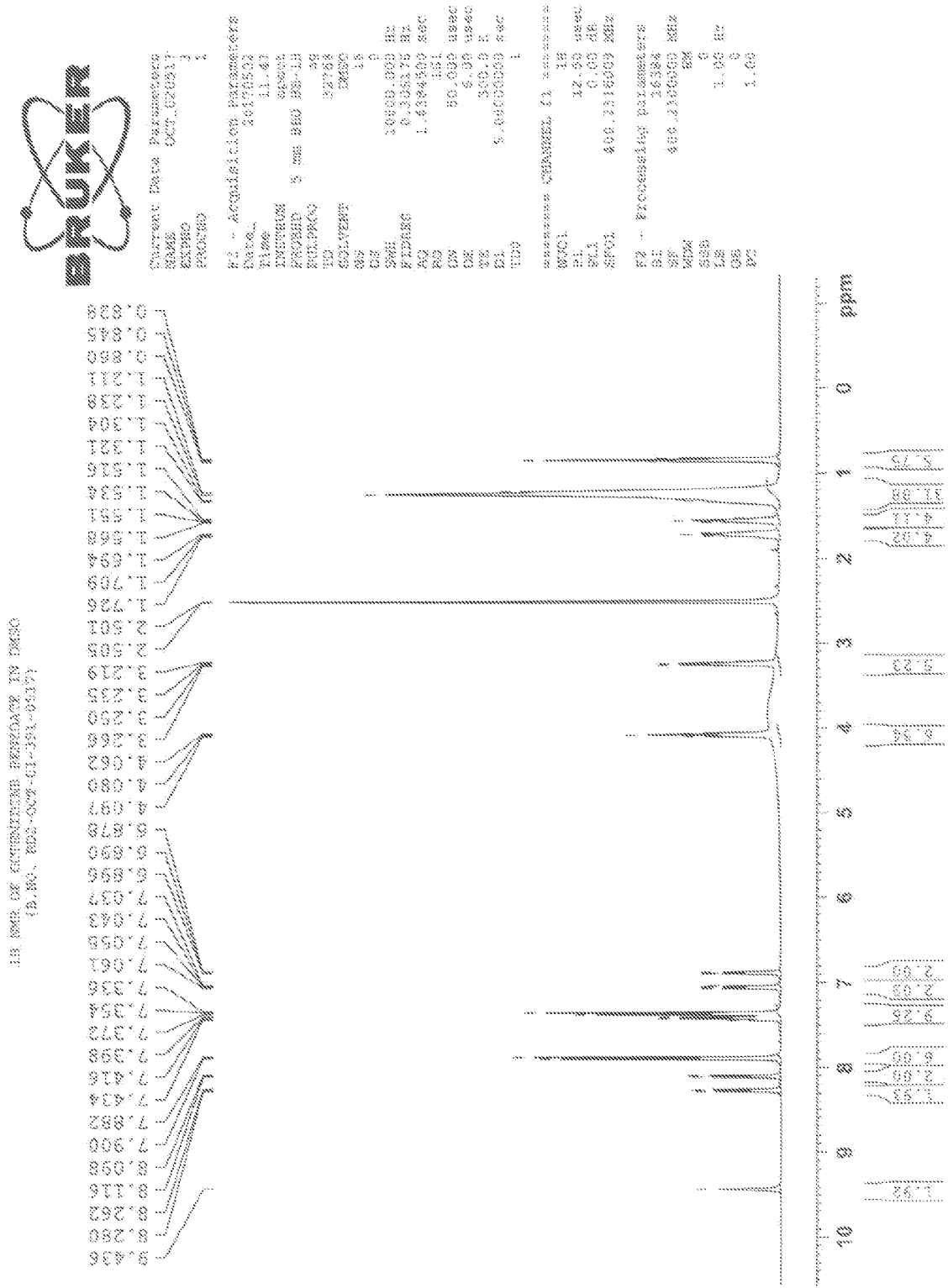

FIG. 2. The crystalline form of Octenidine benzoate salt having Nuclear Magnetic Resonance.

Figure 3:
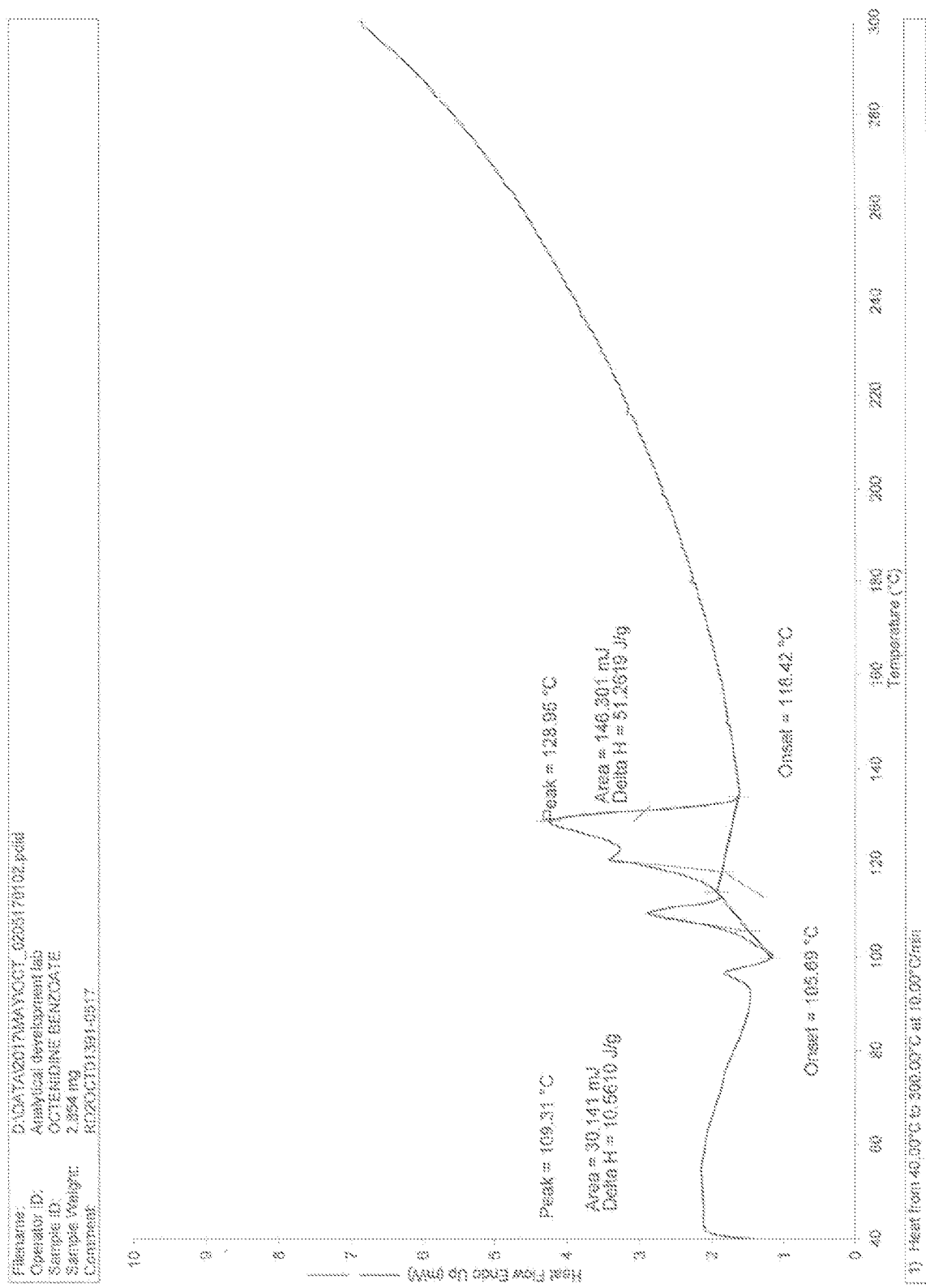

FIG. 3. The crystalline form of Octenidine benzoate salt having a differential scanning calorimetry analysis.

Figure 4:
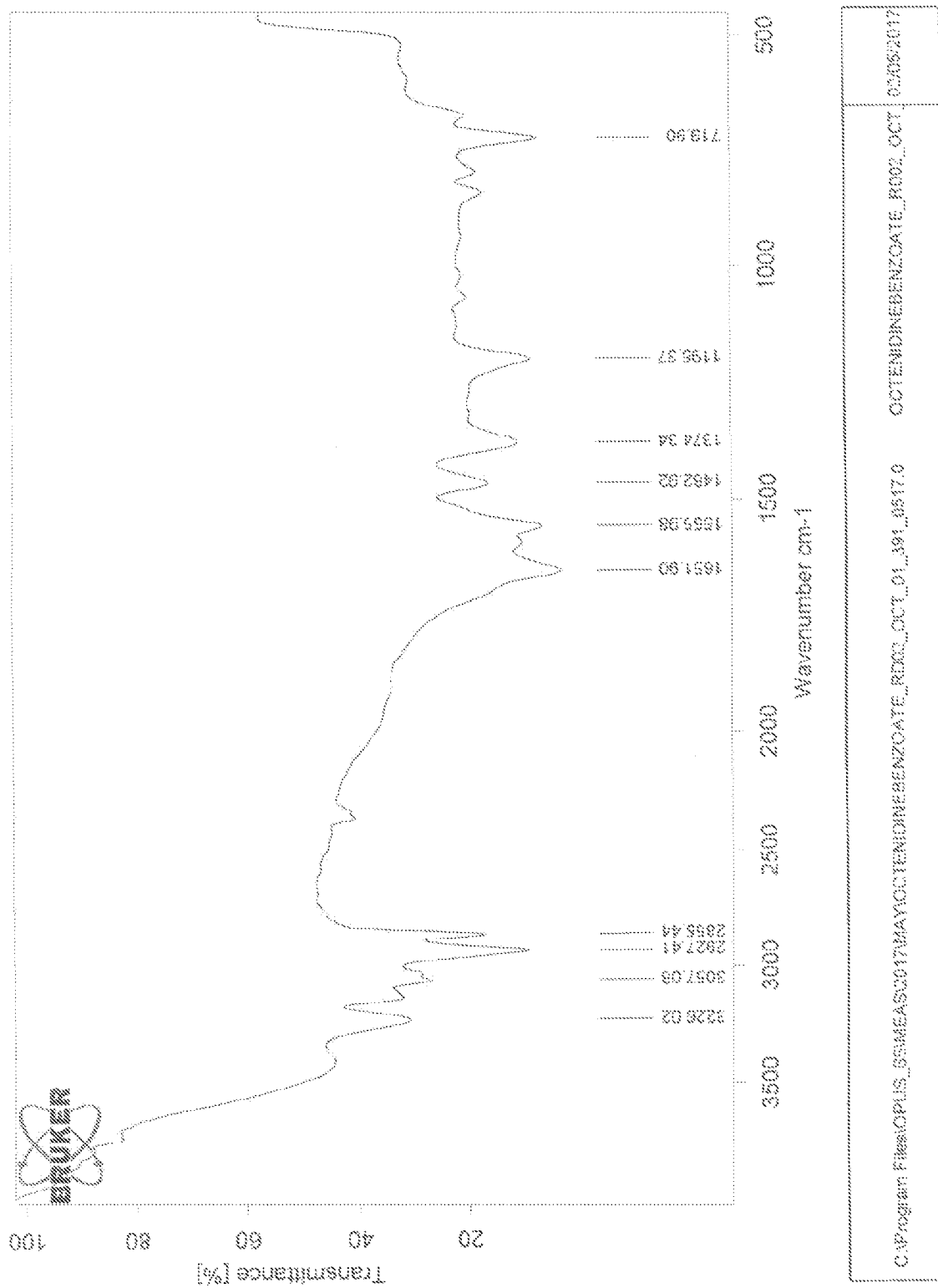

FIG. 4. The crystalline form of Octenidine benzoate salt having a infrared absorption spectrum analysis.

Figure 5:
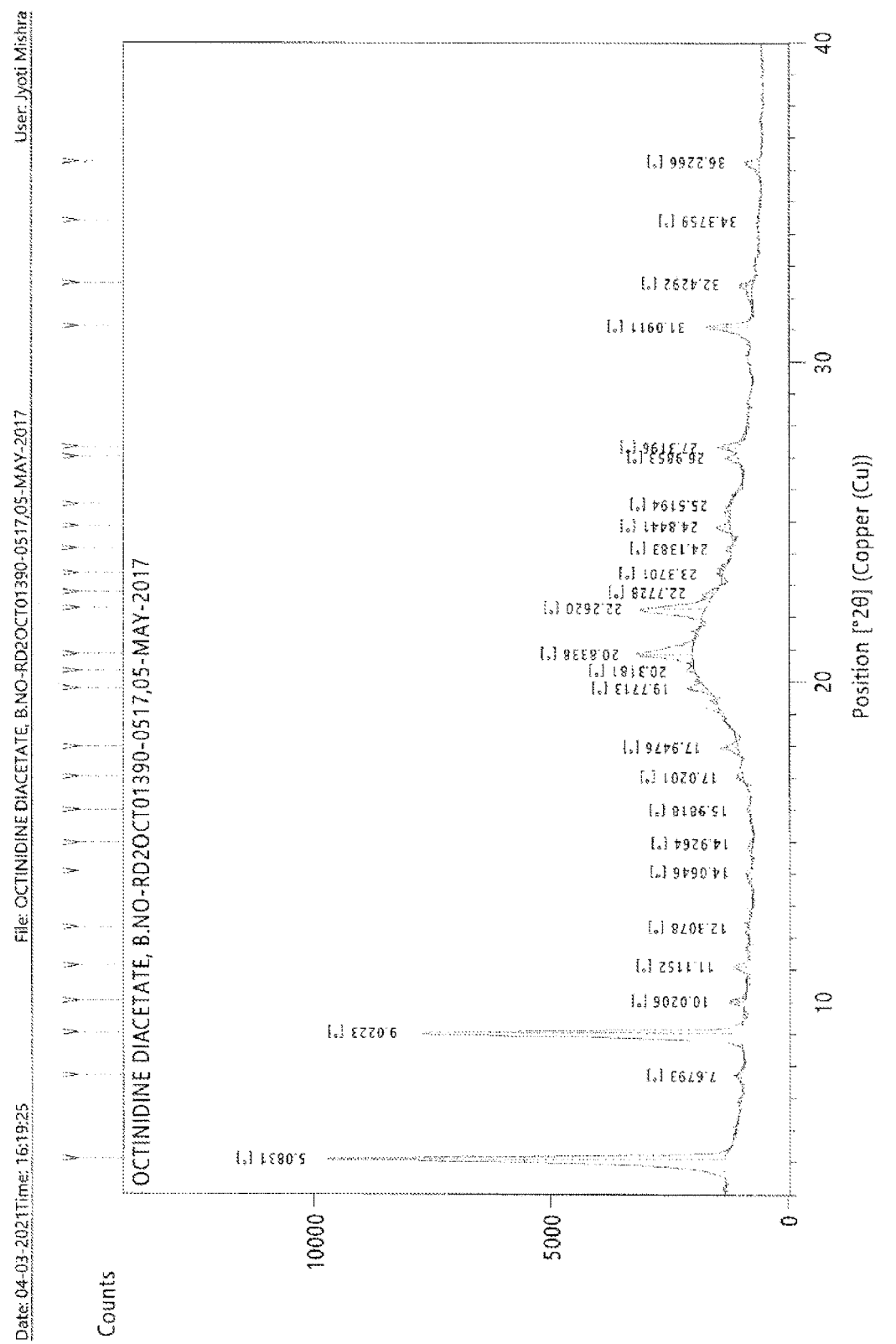

FIG. 5. The crystalline form of Octenidine acetate having crystalline form has an X-ray powder diffraction pattern.

Figure 6:
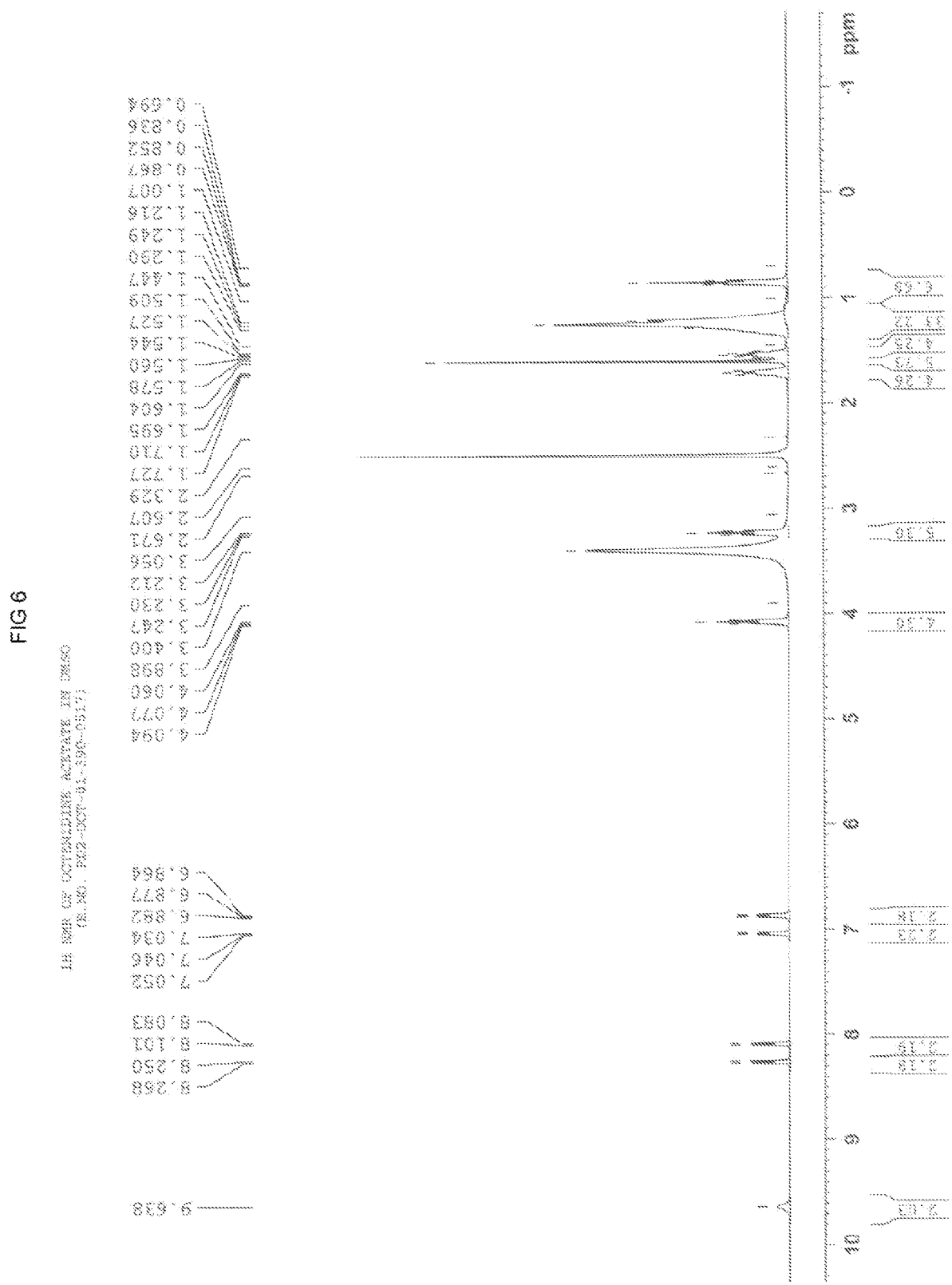

FIG. 6. The crystalline form of Octenidine acetate salt having Nuclear Magnetic Resonance.

Figure 7:
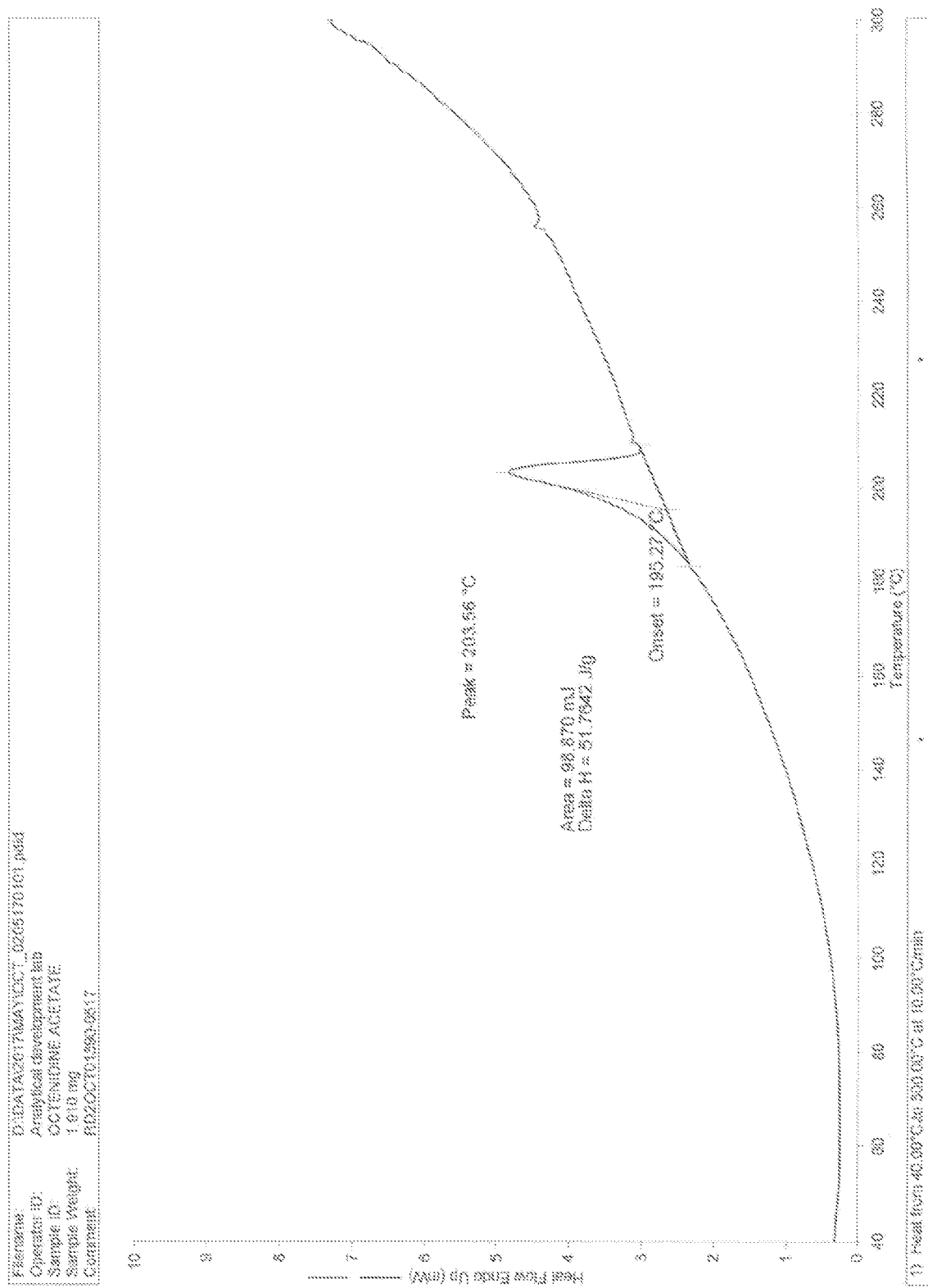

FIG. 7. The crystalline form of Octenidine acetate having a differential scanning calorimetry analysis.

Figure 8:
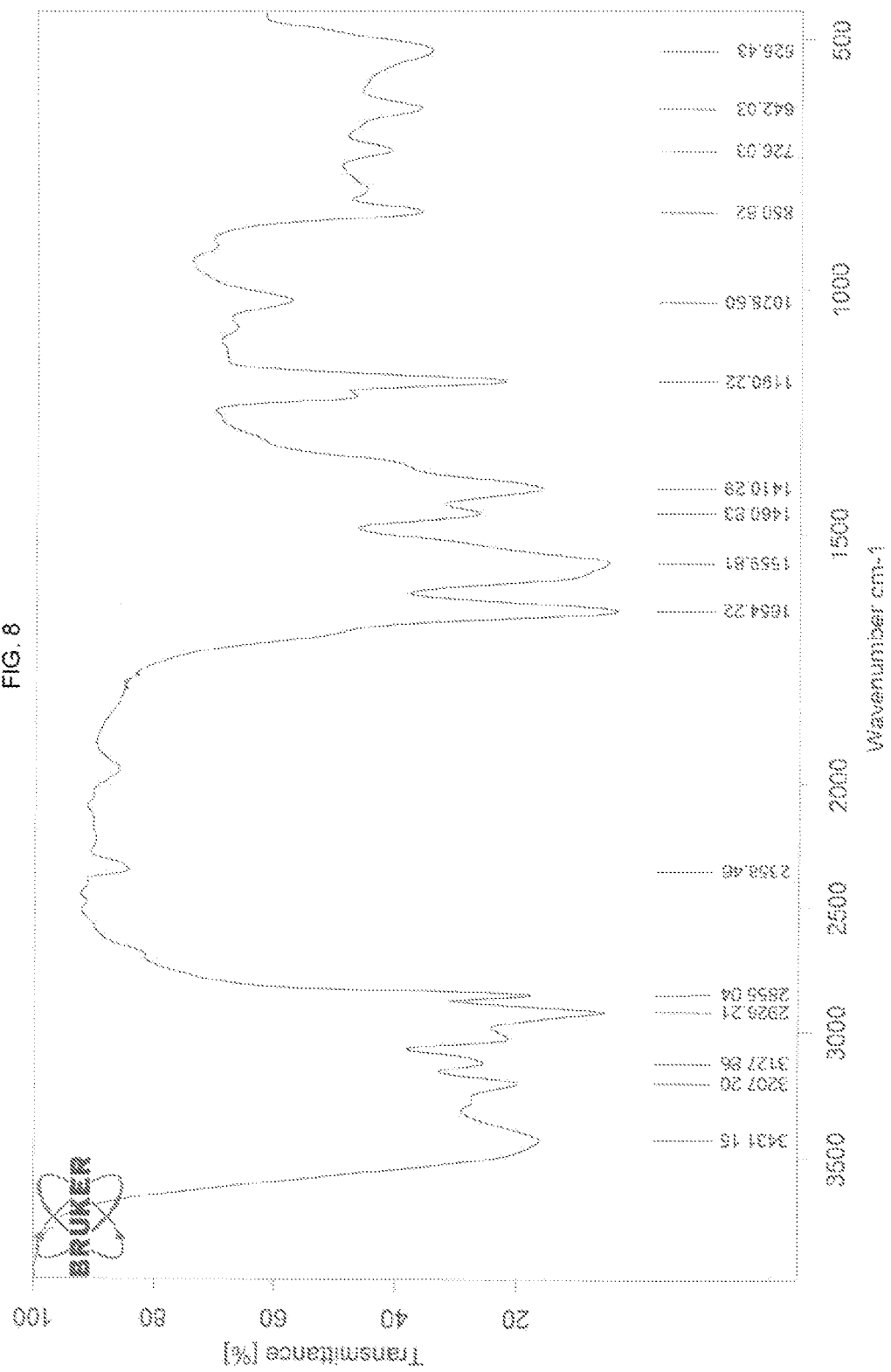

FIG. 8. The crystalline form of Octenidine acetate having a infrared absorption spectrum analysis.

Figure 9:
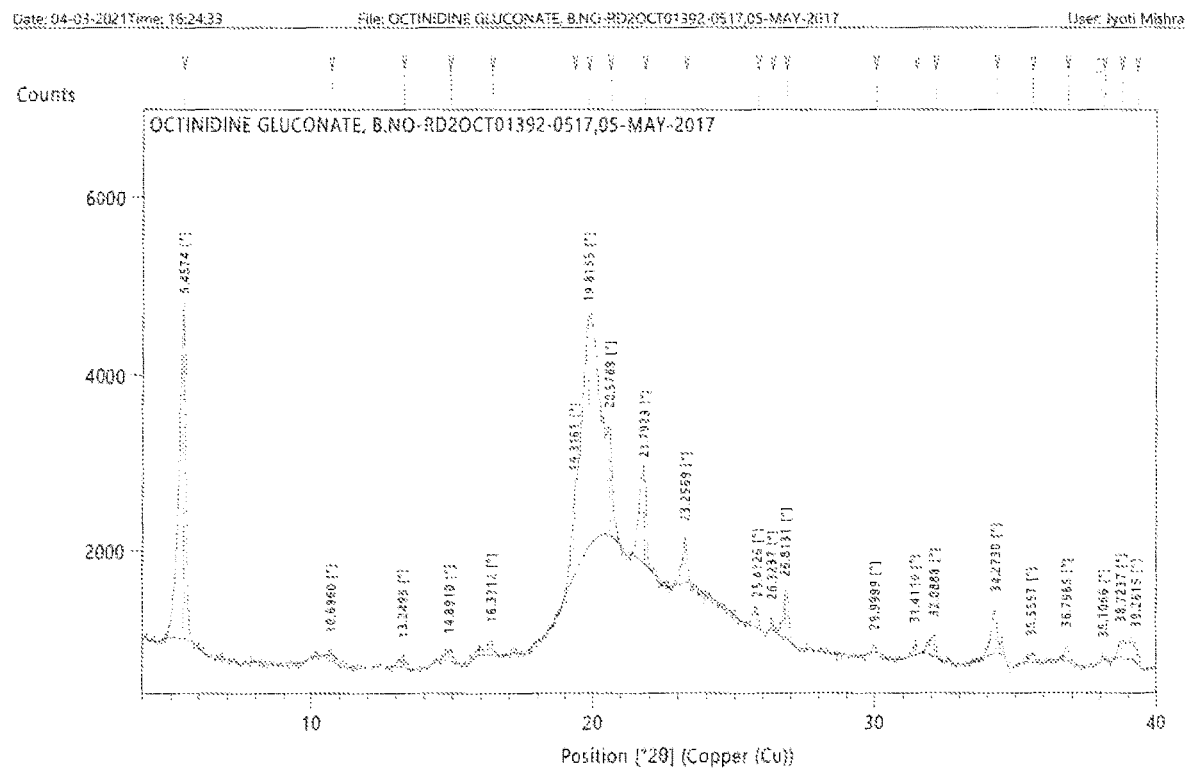

FIG. 9. The crystalline form of Octenidine gluconate having crystalline form has an X-ray powder diffraction pattern.

Figure 10:
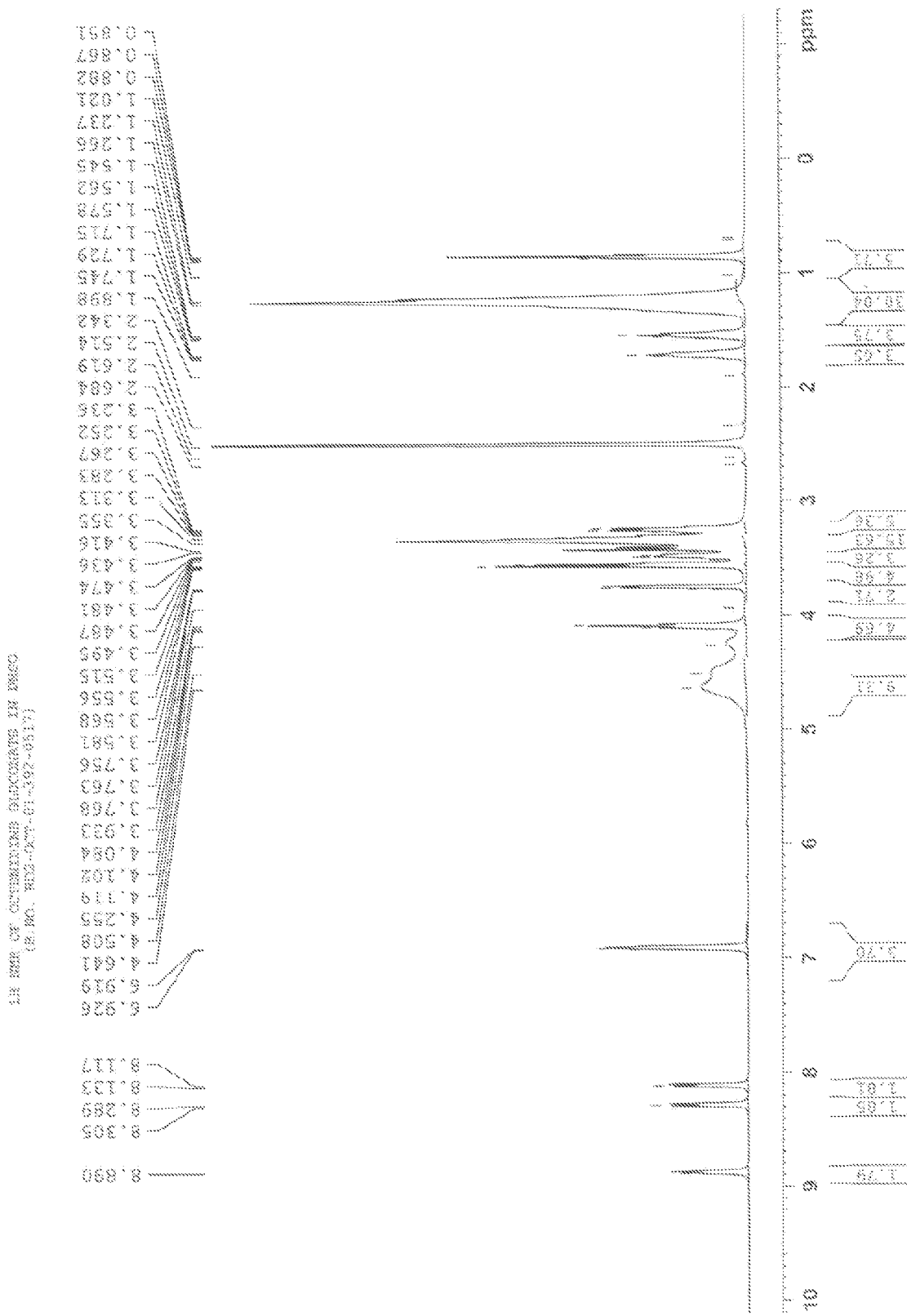

FIG. 10. The crystalline form of Octenidine gluconate salt having Nuclear Magnetic Resonance.

Figure 11:
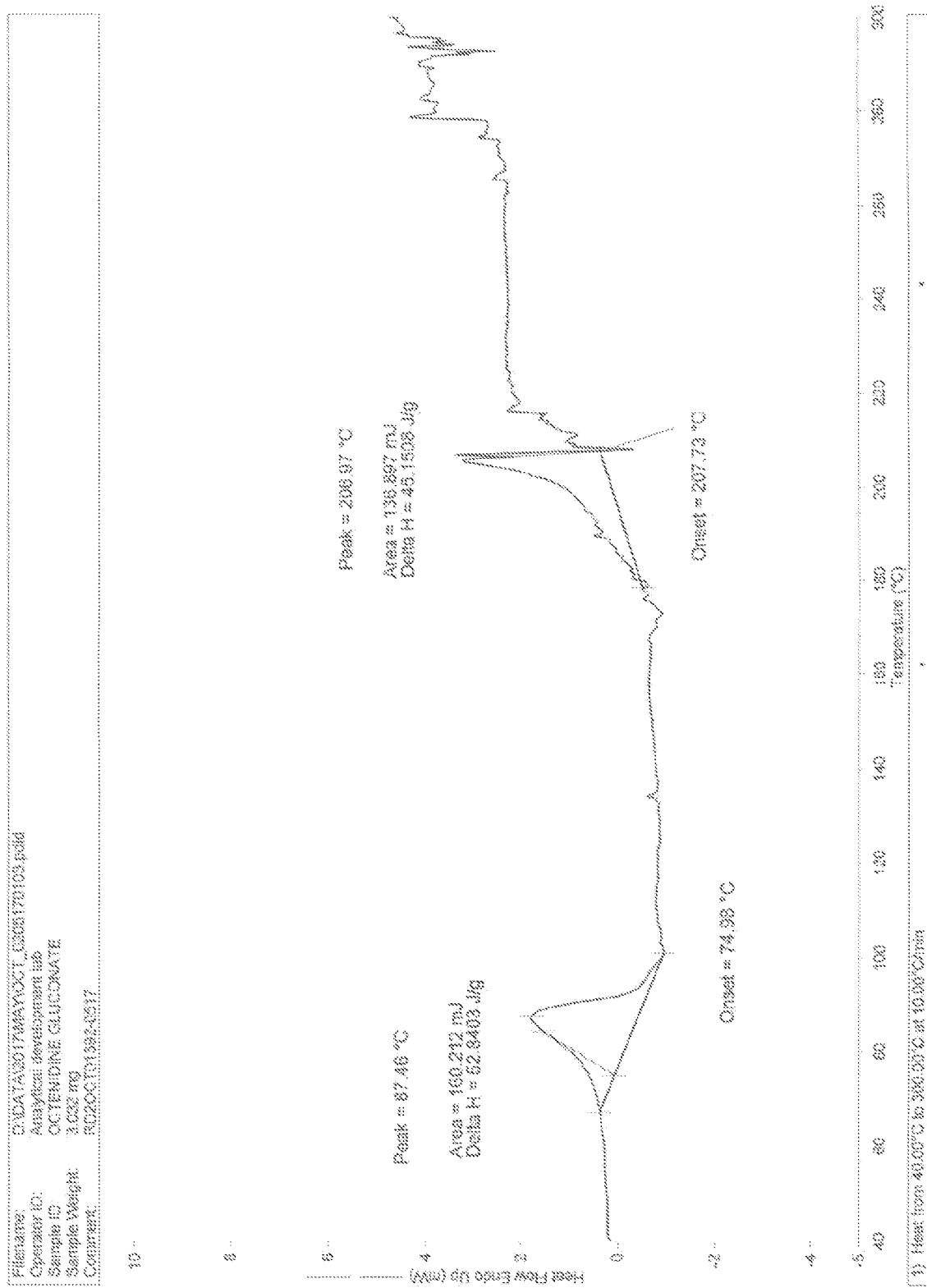

FIG. 11. The crystalline form of Octenidine gluconate having a differential scanning calorimetry analysis.

Figure 12:
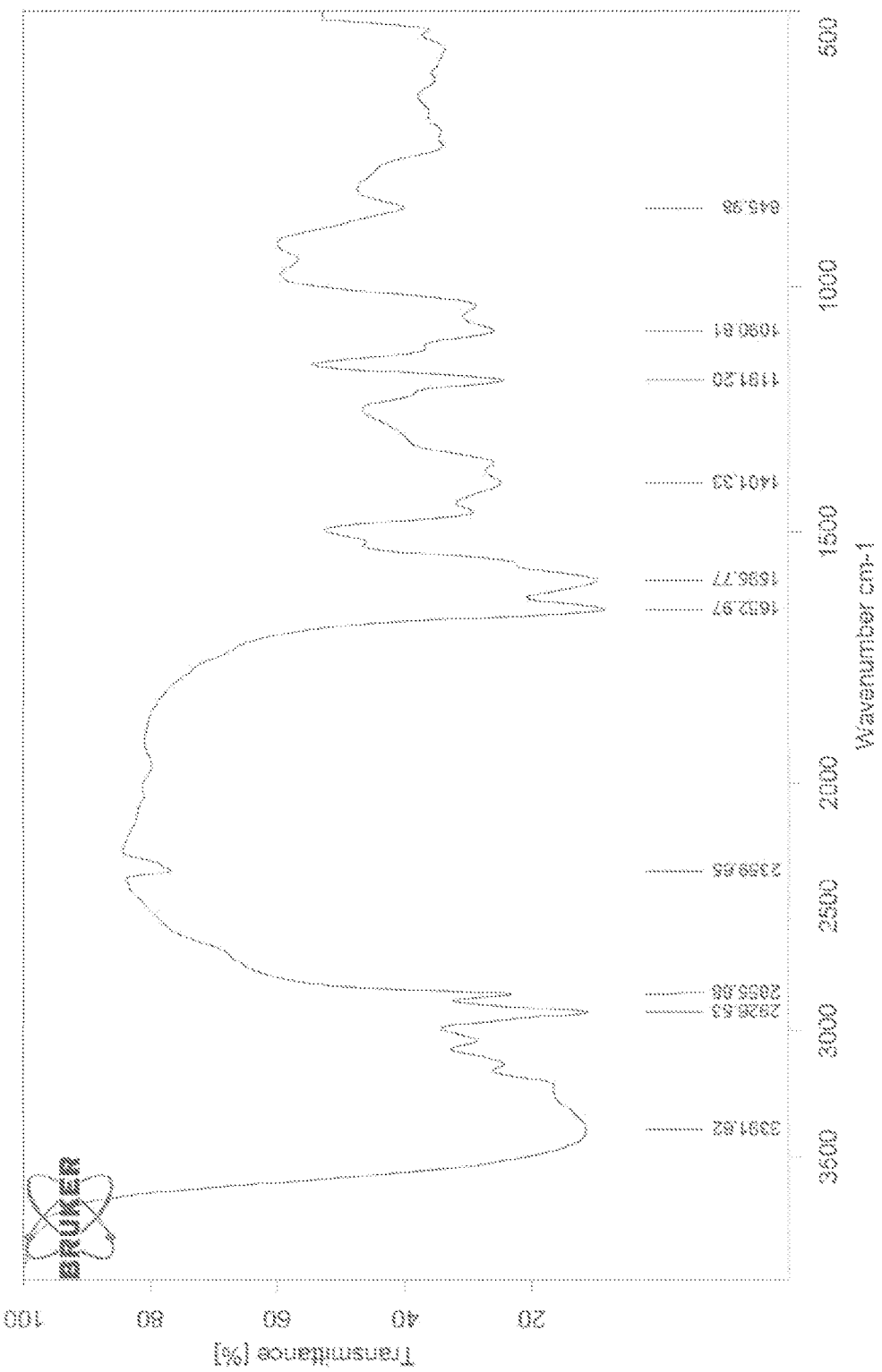

FIG. 12. The crystalline form of Octenidine gluconate having a infrared absorption spectrum analysis.

Figure 13:
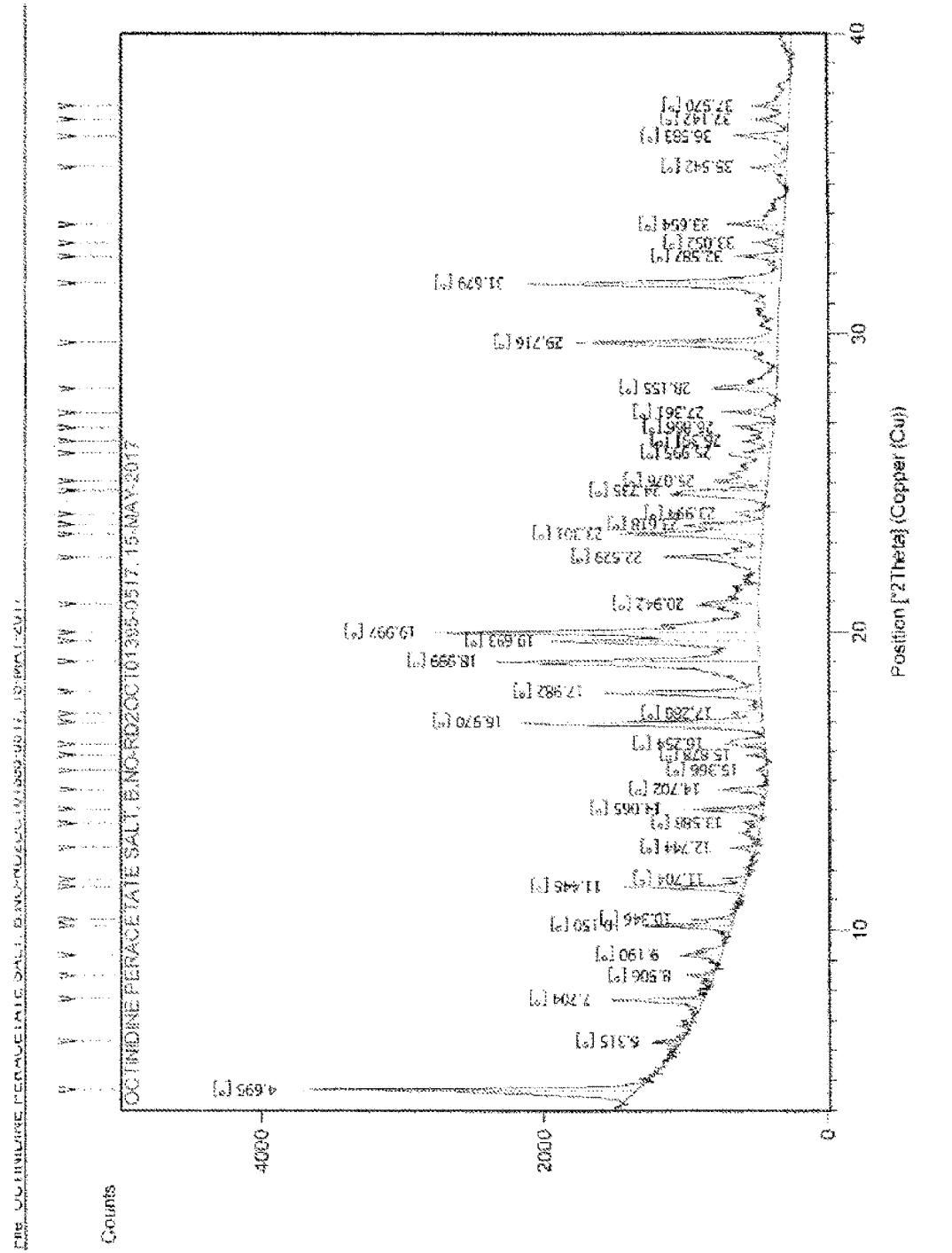

FIG. 13. The crystalline form of Octenidine per acetic acid having crystalline form has an X-ray powder diffraction pattern.

Figure 14:
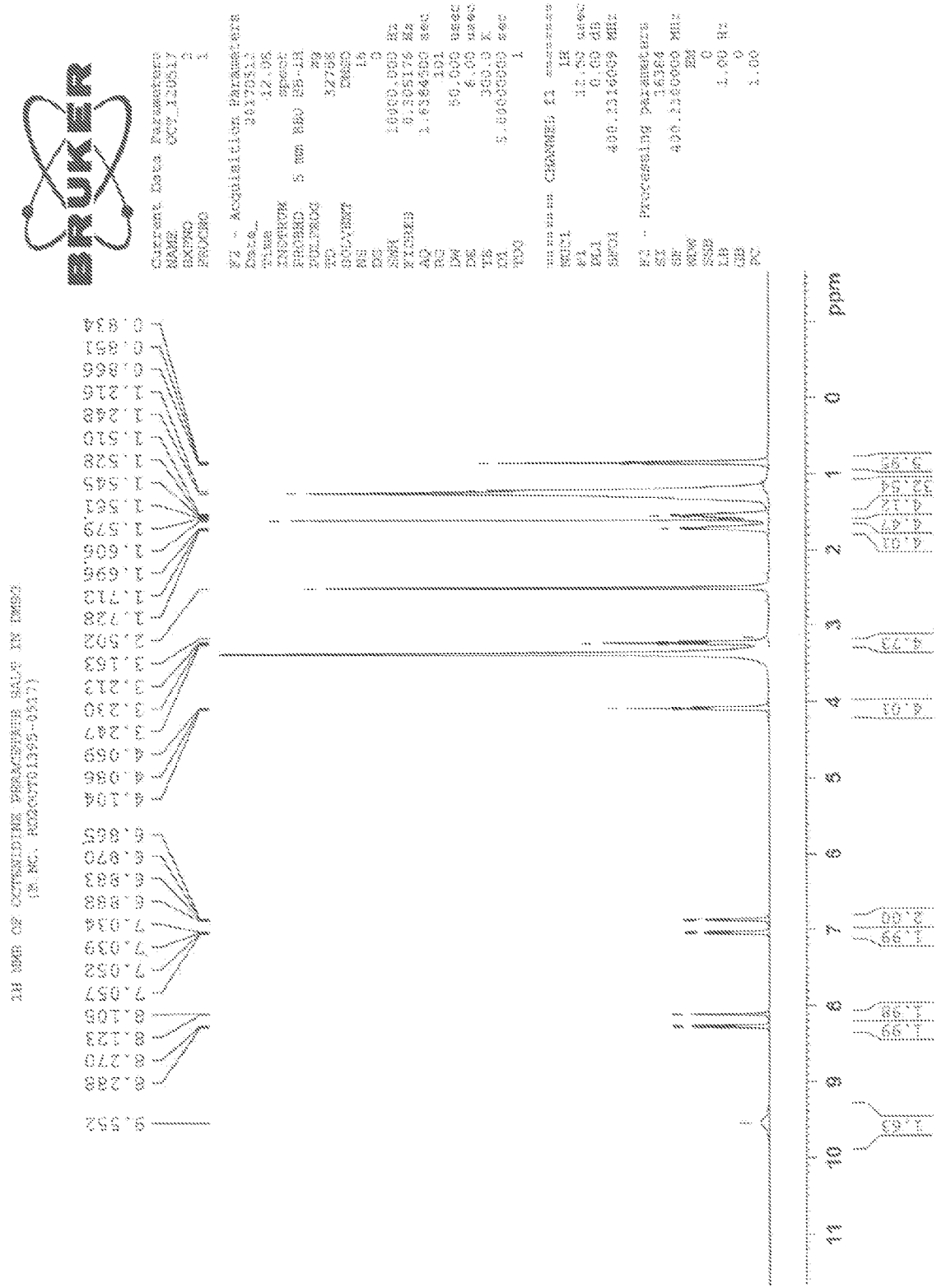

FIG. 14. The crystalline form of Octenidine per acetic acid salt having Nuclear Magnetic Resonance.

Figure 15:
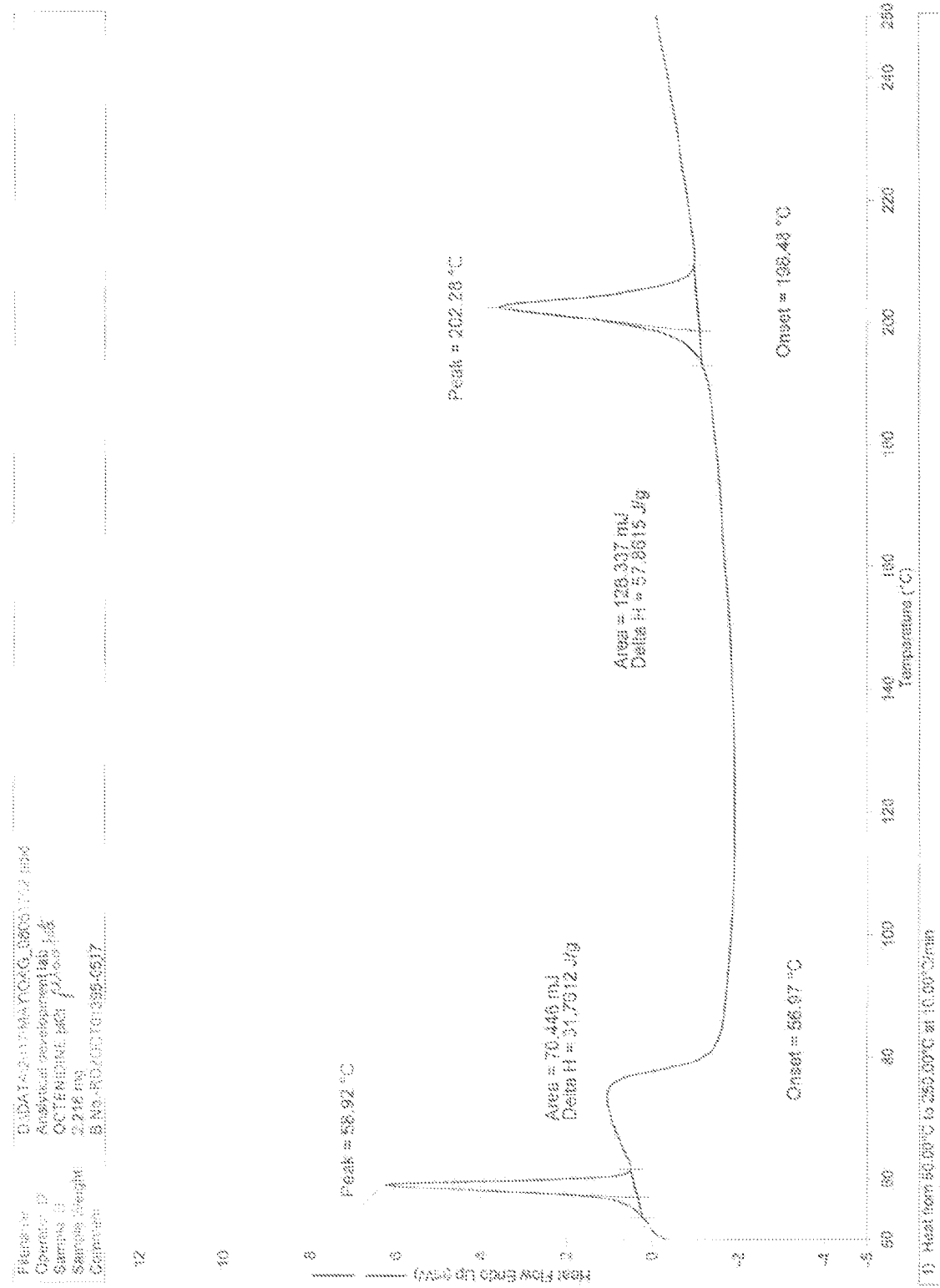

FIG. 15. The crystalline form of Octenidine per acetic acid having a differential scanning calorimetry analysis.

Figure 16:
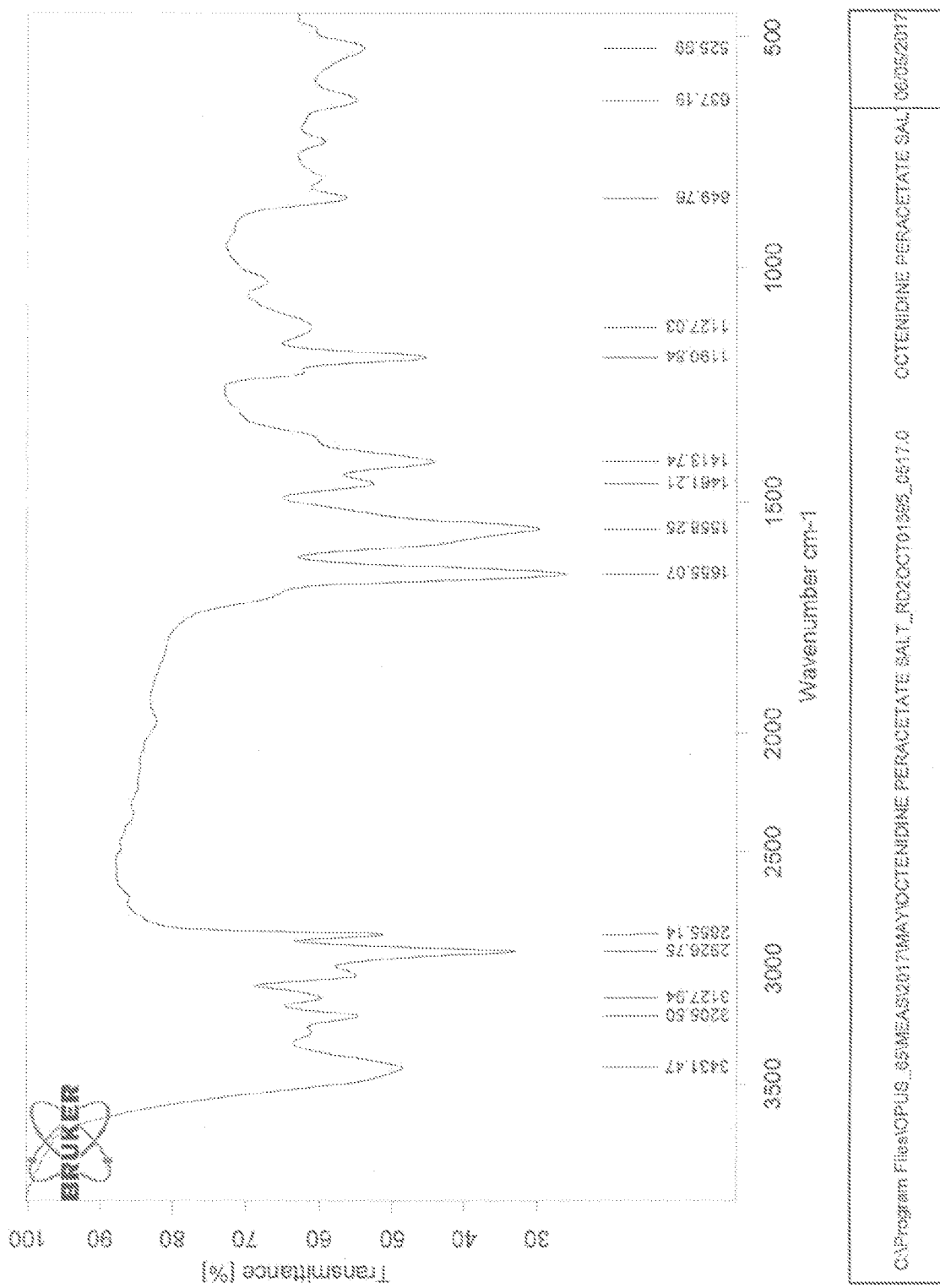

FIG. 16. The crystalline form of Octenidine per acetic acid having a infrared absorption spectrum analysis.

Figure 17:
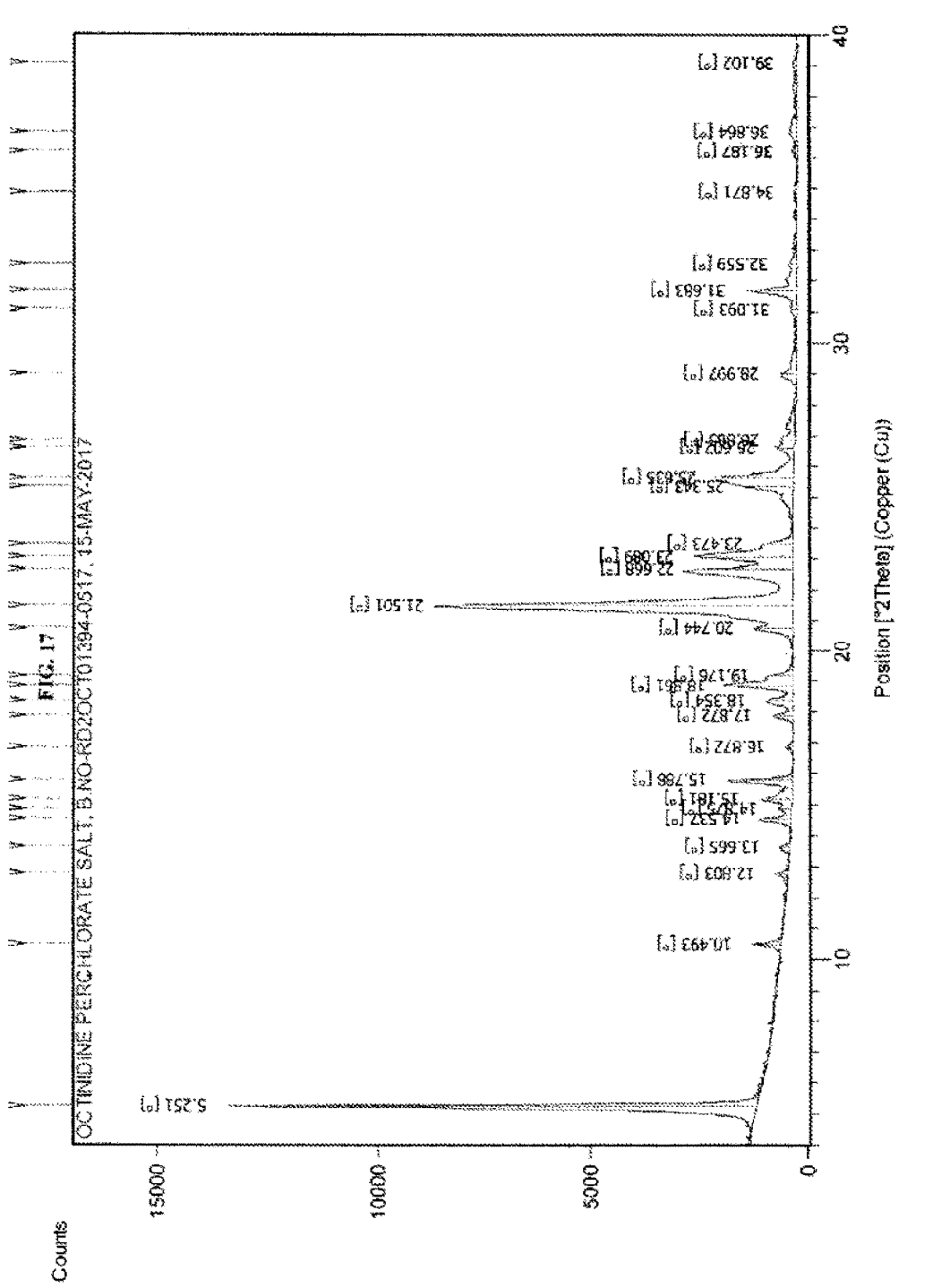

FIG. 17. The crystalline form of Octenidine perchloric acid having crystalline form has an X-ray powder diffraction pattern.

Figure 18:
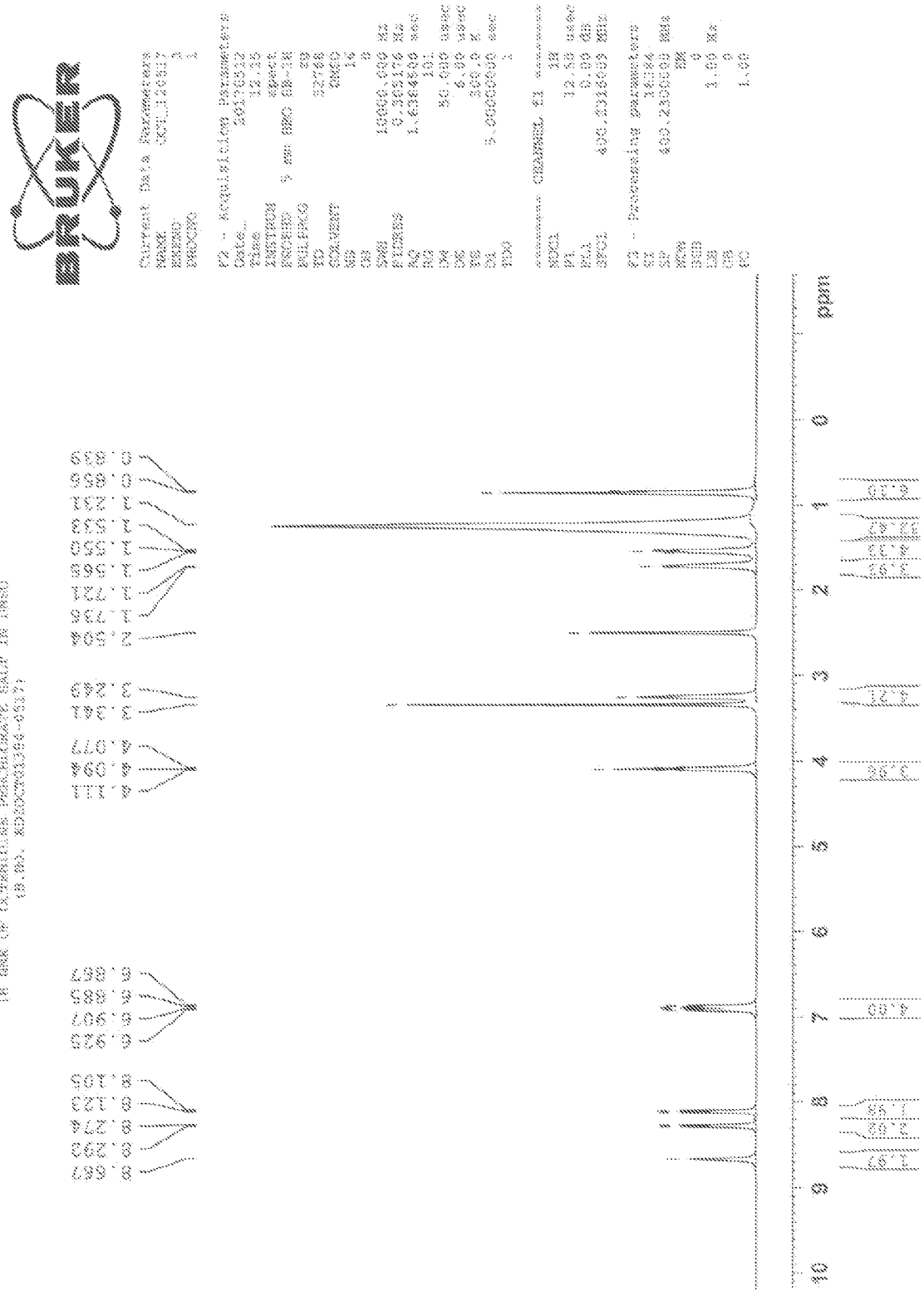

FIG. 18. The crystalline form of Octenidine perchloric salt having Nuclear Magnetic Resonance.

Figure 19:
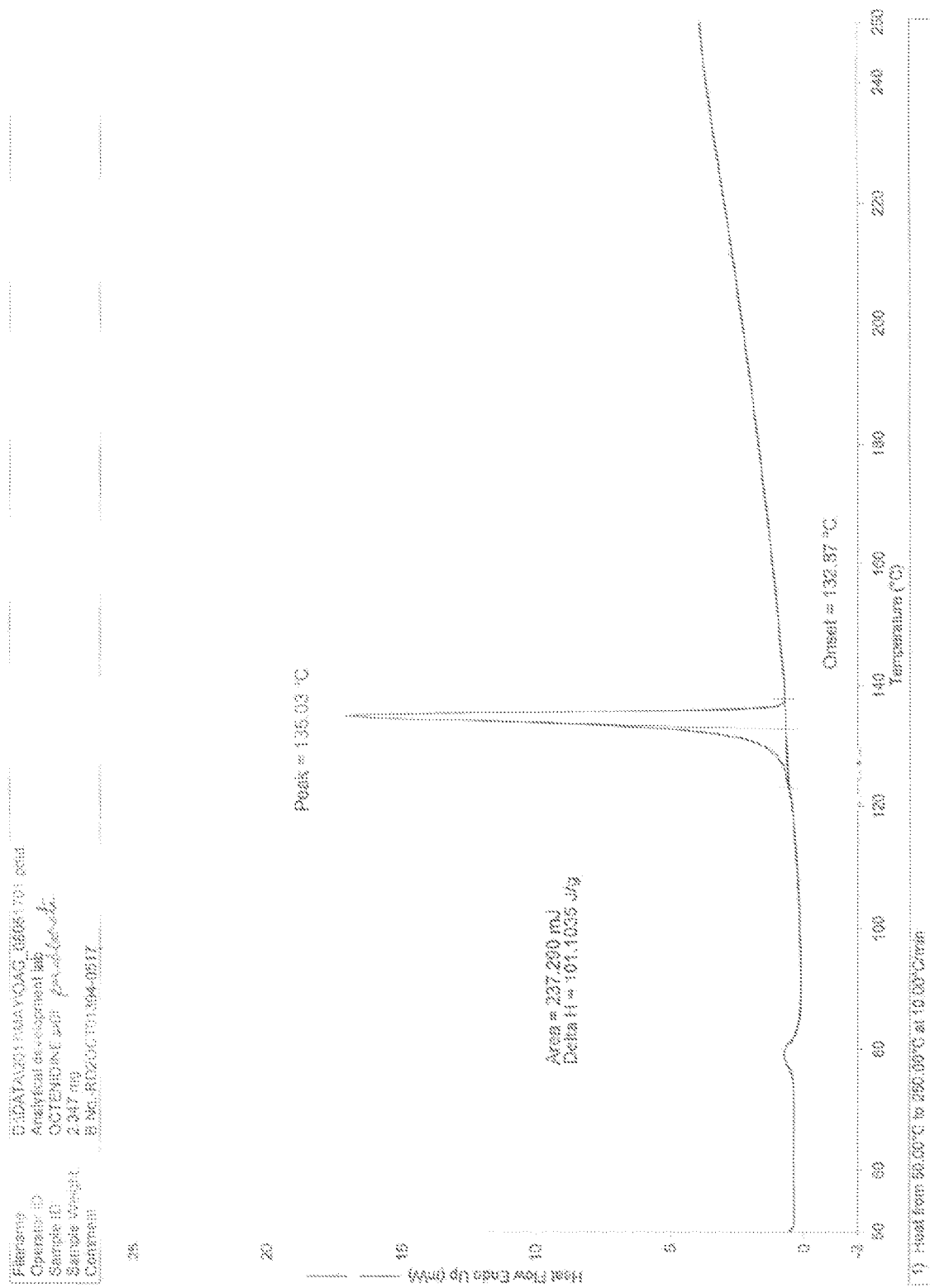

FIG. 19. The crystalline form of Octenidine perchloric acid having a differential scanning calorimetry analysis.

Figure 20:
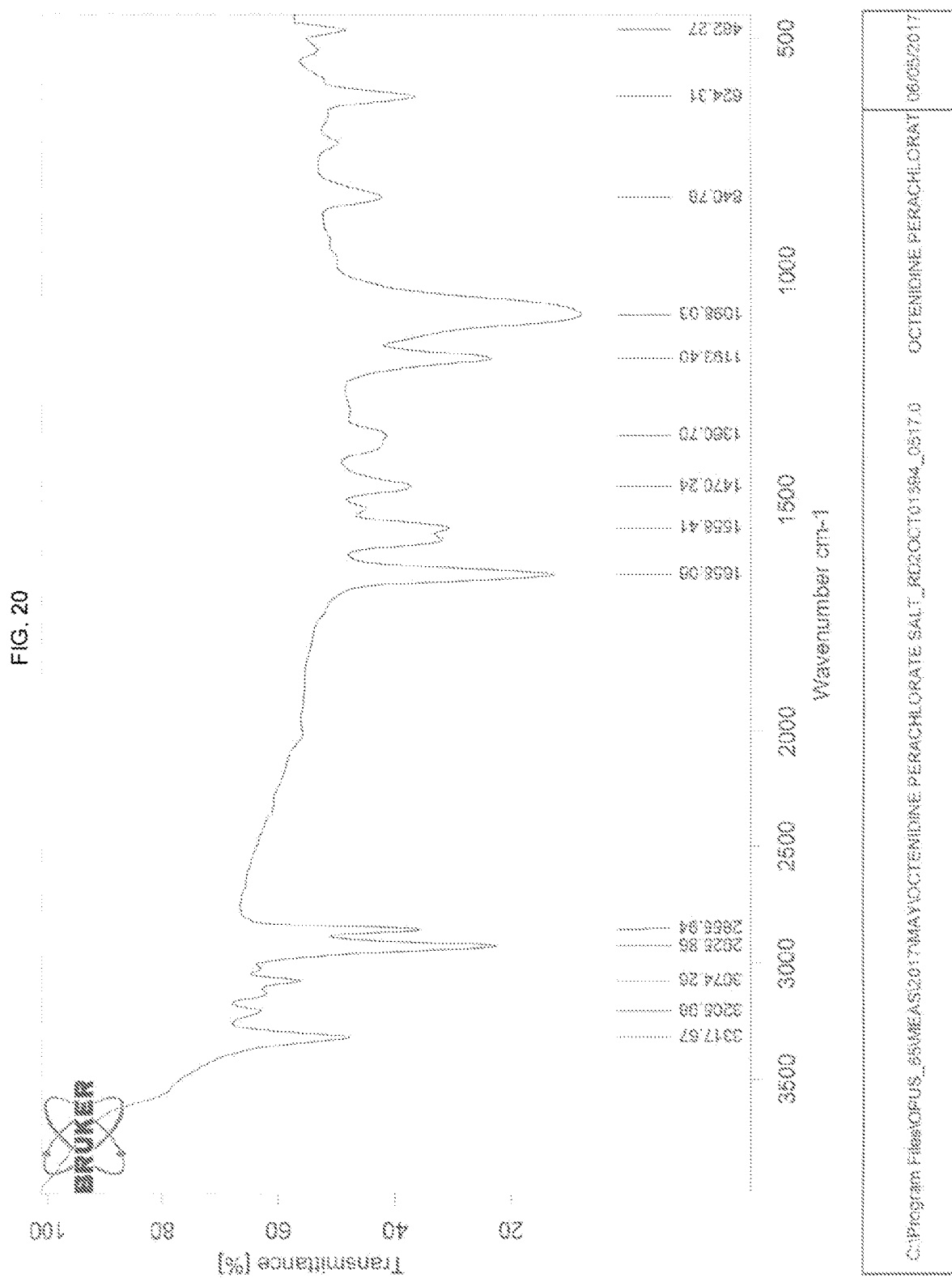

FIG. 20. The crystalline form of Octenidine perchloric acid having a infrared absorption spectrum analysis.

Figure 21:
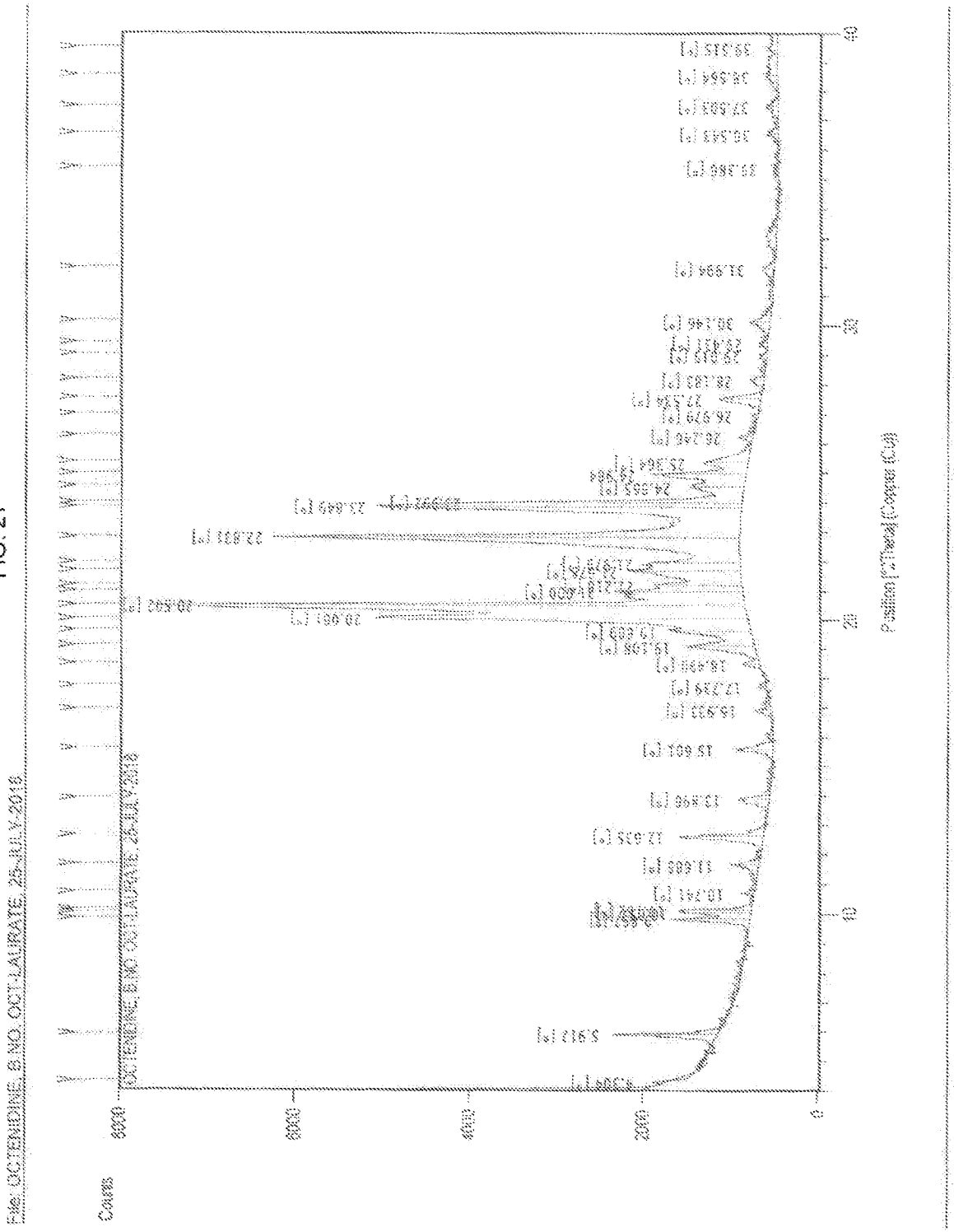

FIG. 21. The crystalline form of Octenidine lauric acid having crystalline form has an X-ray powder diffraction pattern.

Figure 22:
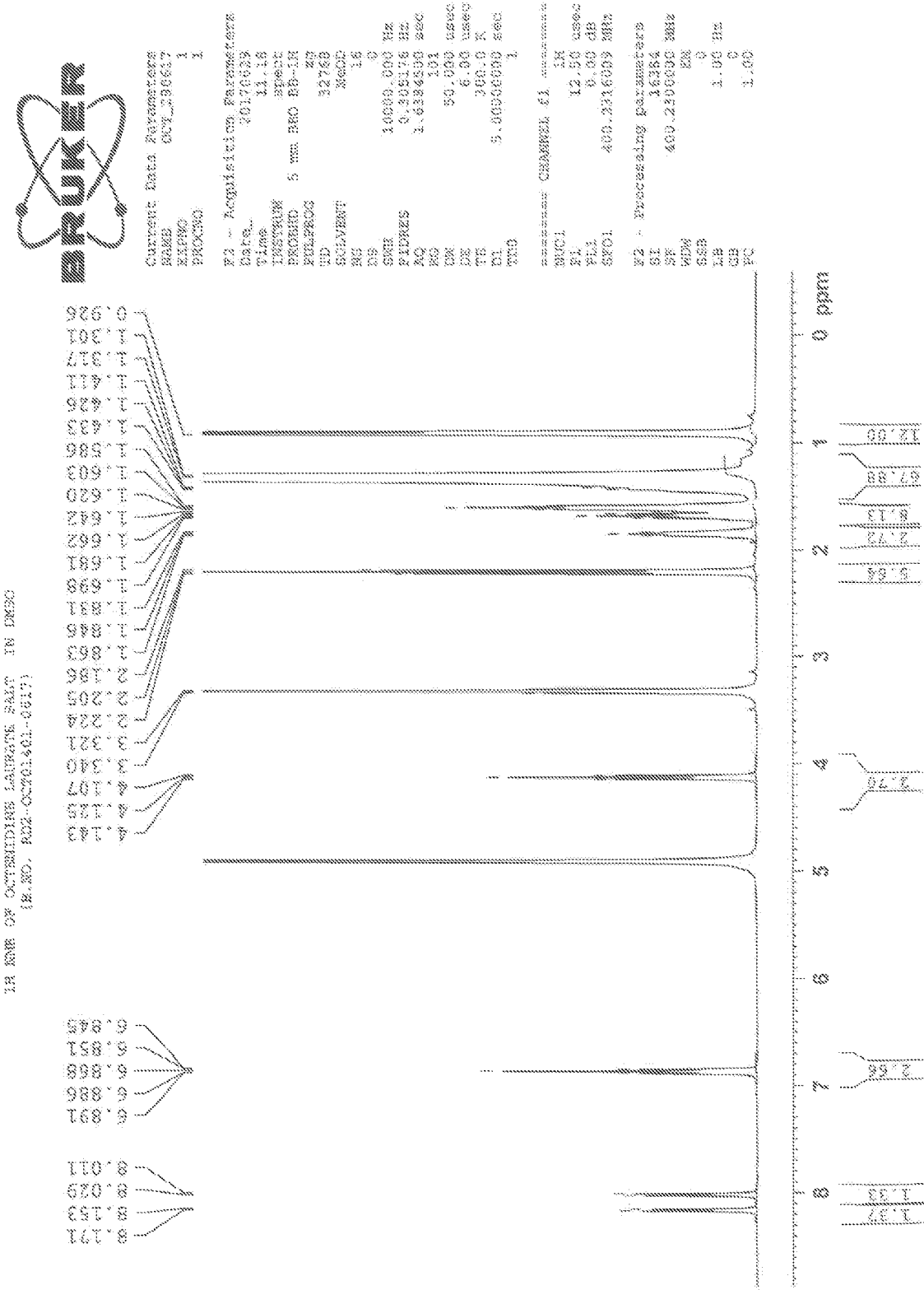

FIG. 22. The crystalline form of Octenidine lauric acid salt having Nuclear Magnetic Resonance.

Figure 23:
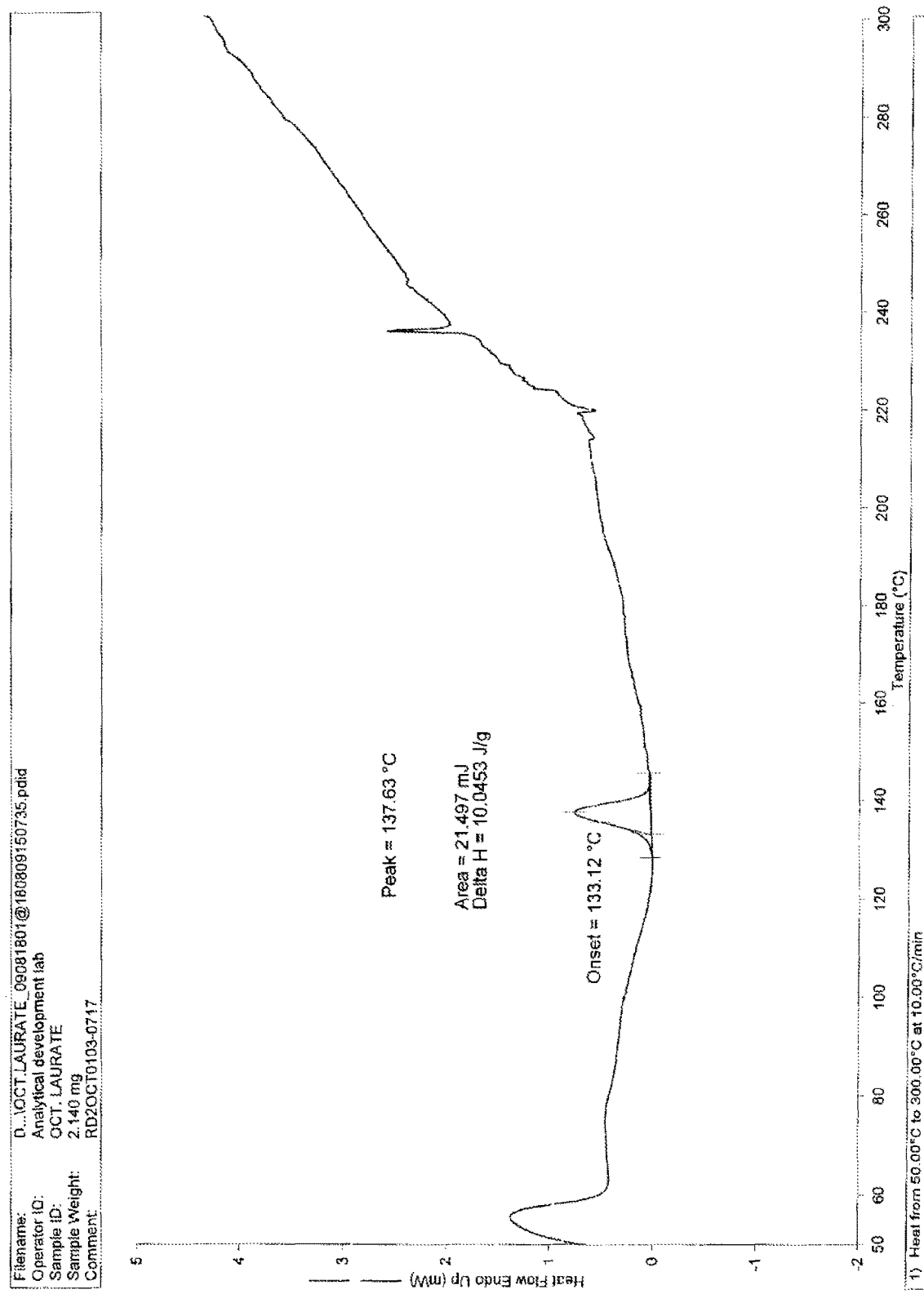

FIG. 23. The crystalline form of Octenidine lauric acid having a differential scanning calorimetry analysis.

Figure 24:
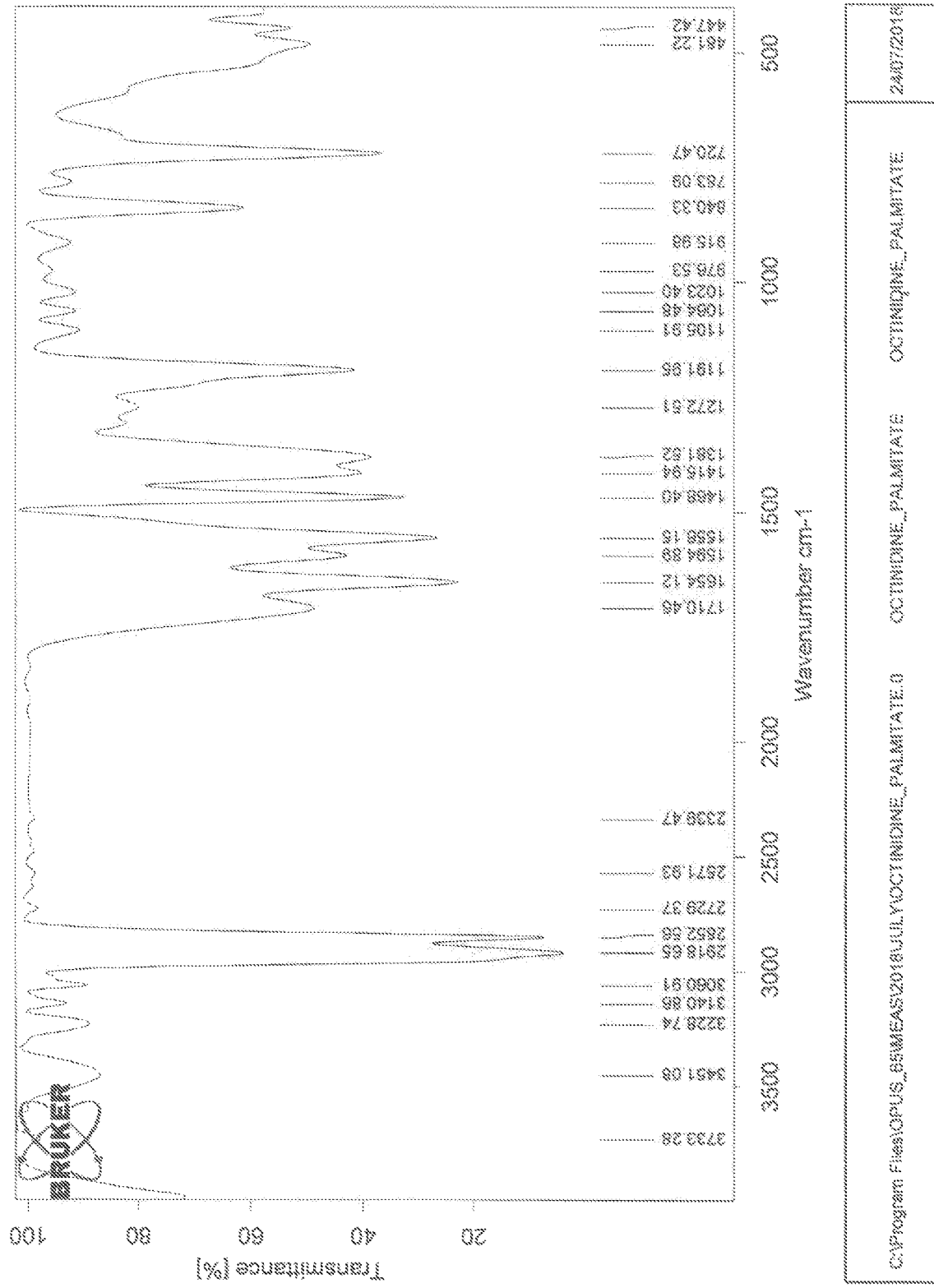

FIG. 24. The crystalline form of Octenidine lauric acid having a infrared absorption spectrum analysis.

Figure 25:
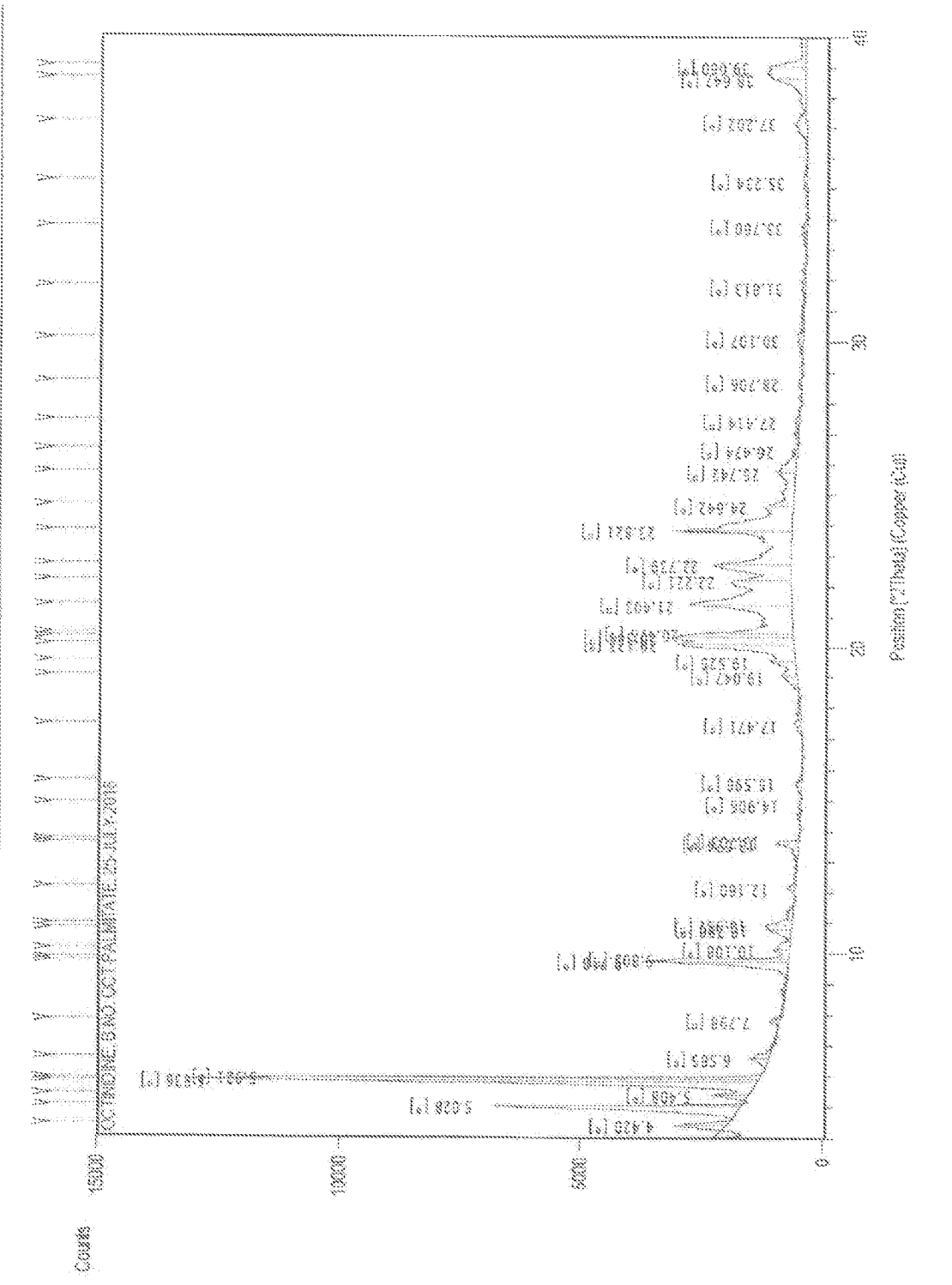

FIG. 25. The crystalline form of Octenidine palmitic acid having crystalline form has an X-ray powder diffraction pattern.

Figure 26:
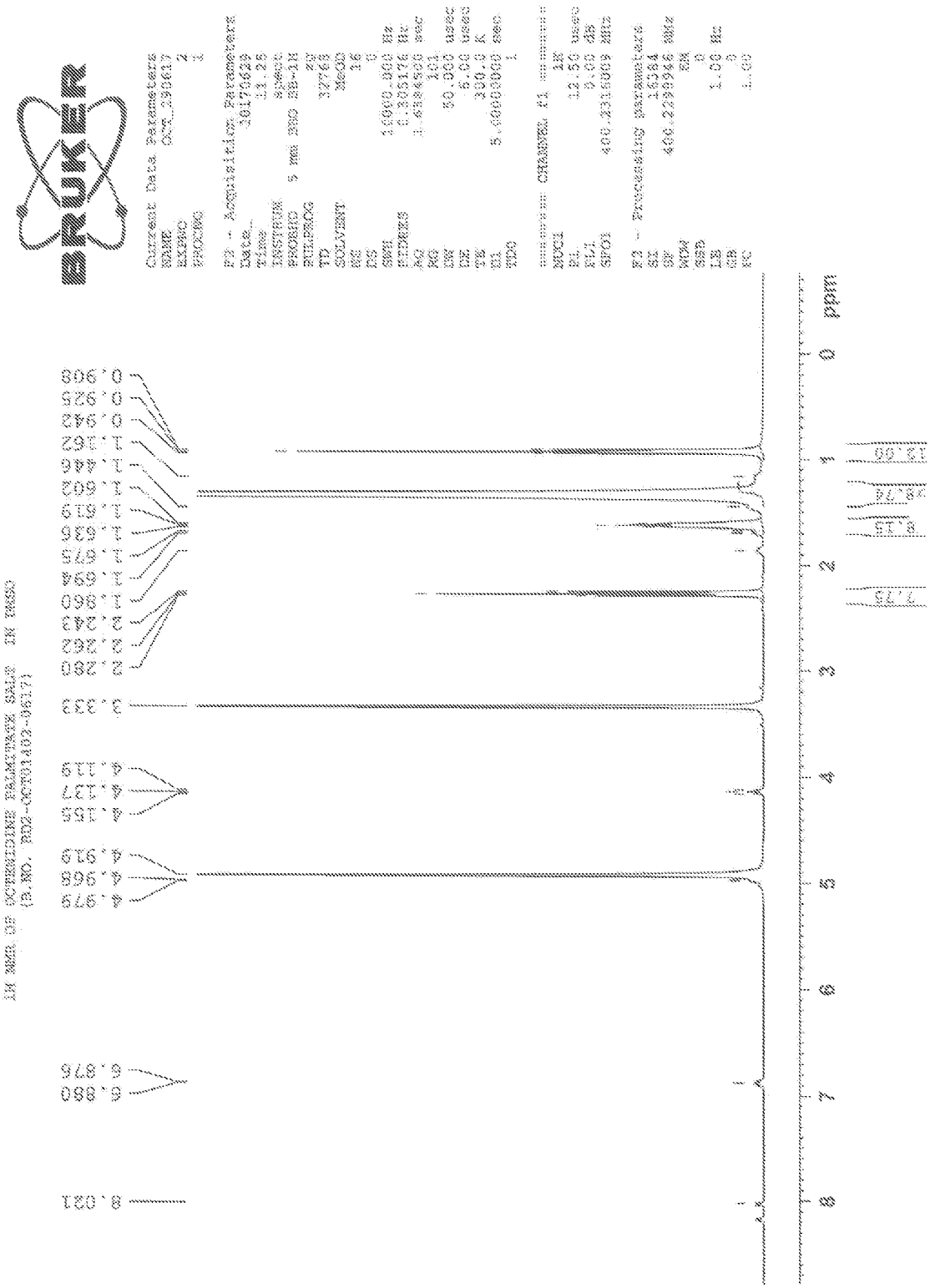

FIG. 26. The crystalline form of Octenidine palmitic acid salt having Nuclear Magnetic Resonance.

Figure 27:
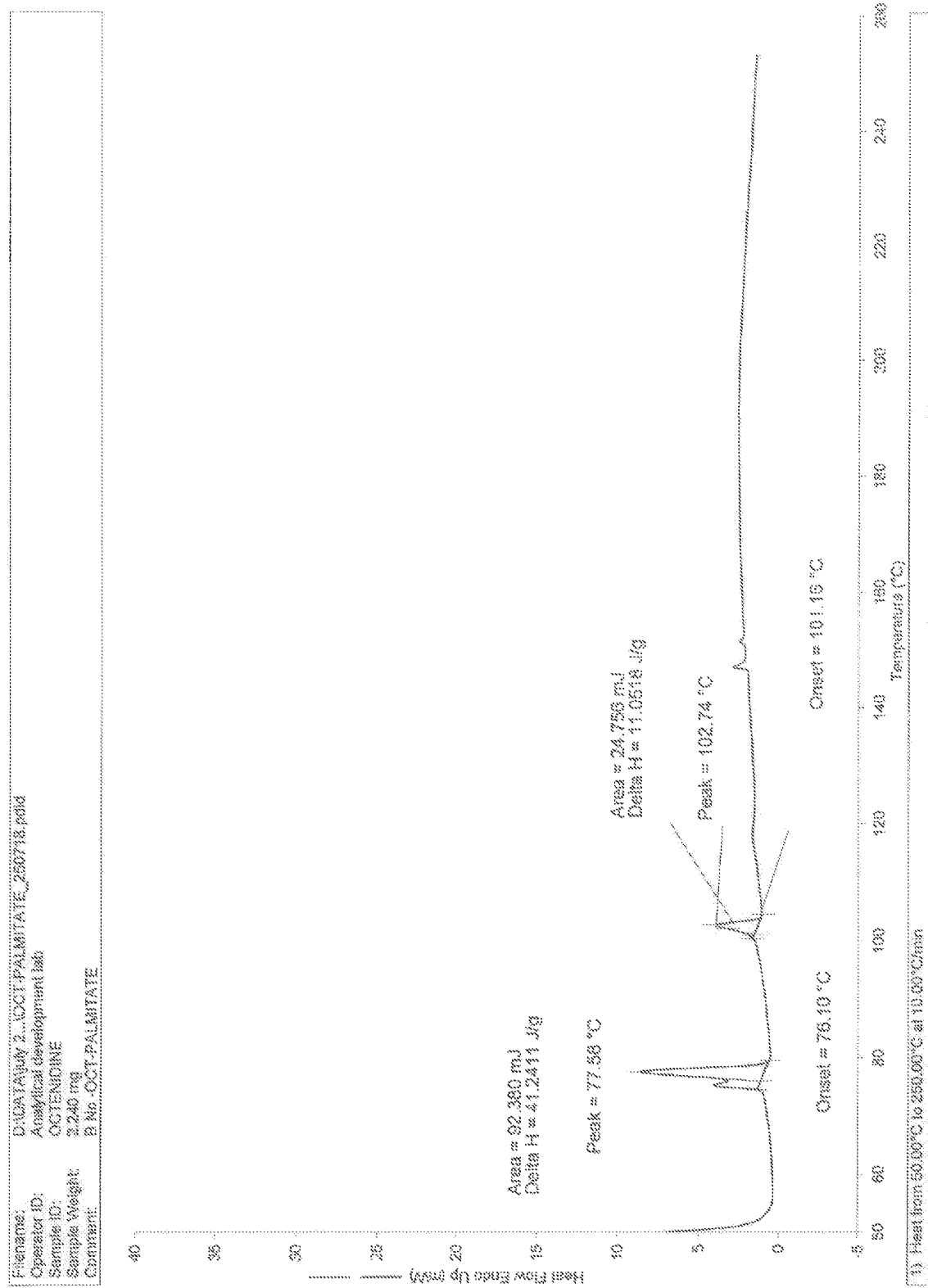

FIG. 27. The crystalline form of Octenidine palmitic acid having a differential scanning calorimetry analysis.

Figure 28:
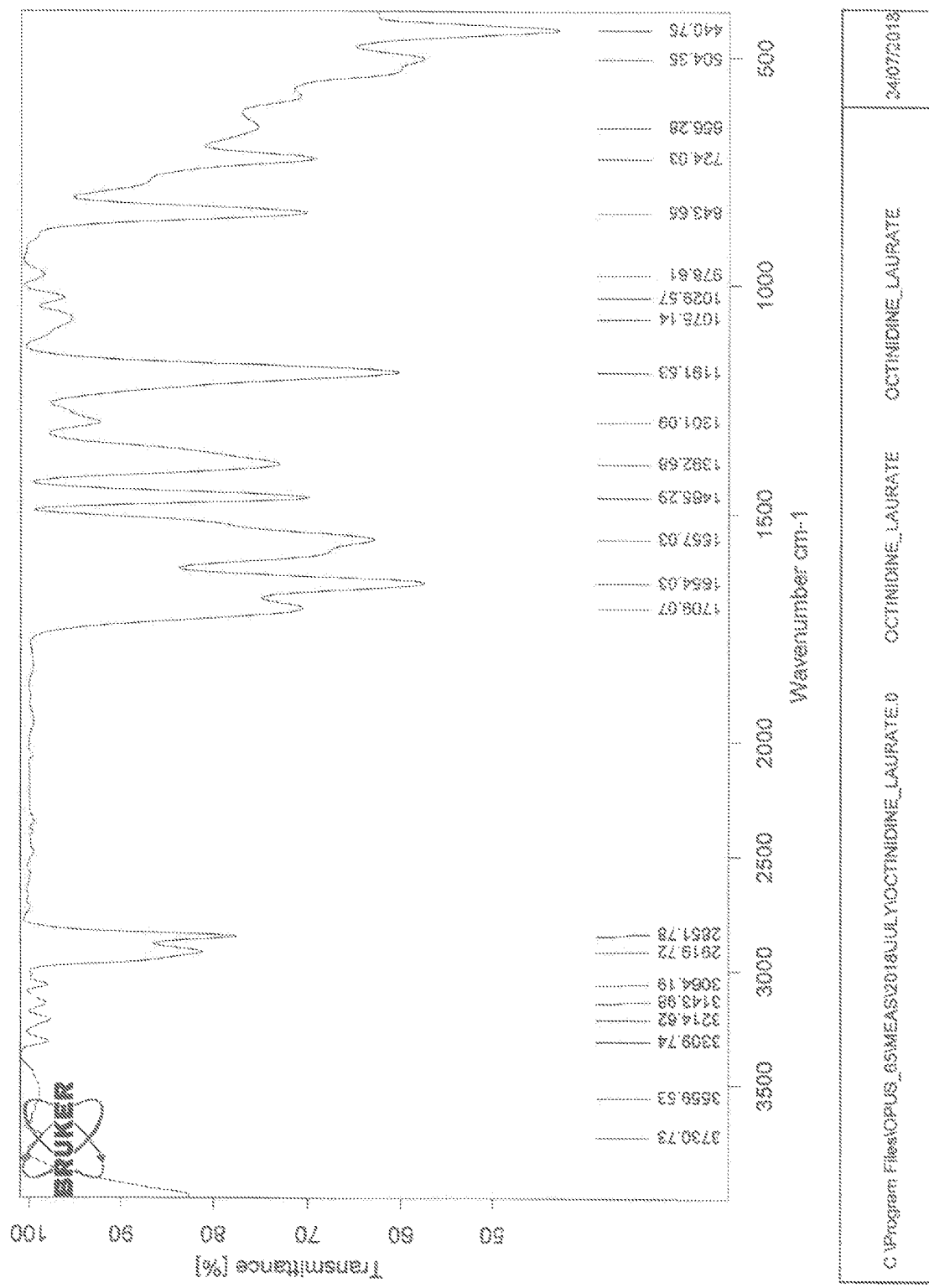

FIG. 28. The crystalline form of Octenidine palmitic acid having a infrared absorption spectrum analysis.

Figure 29:
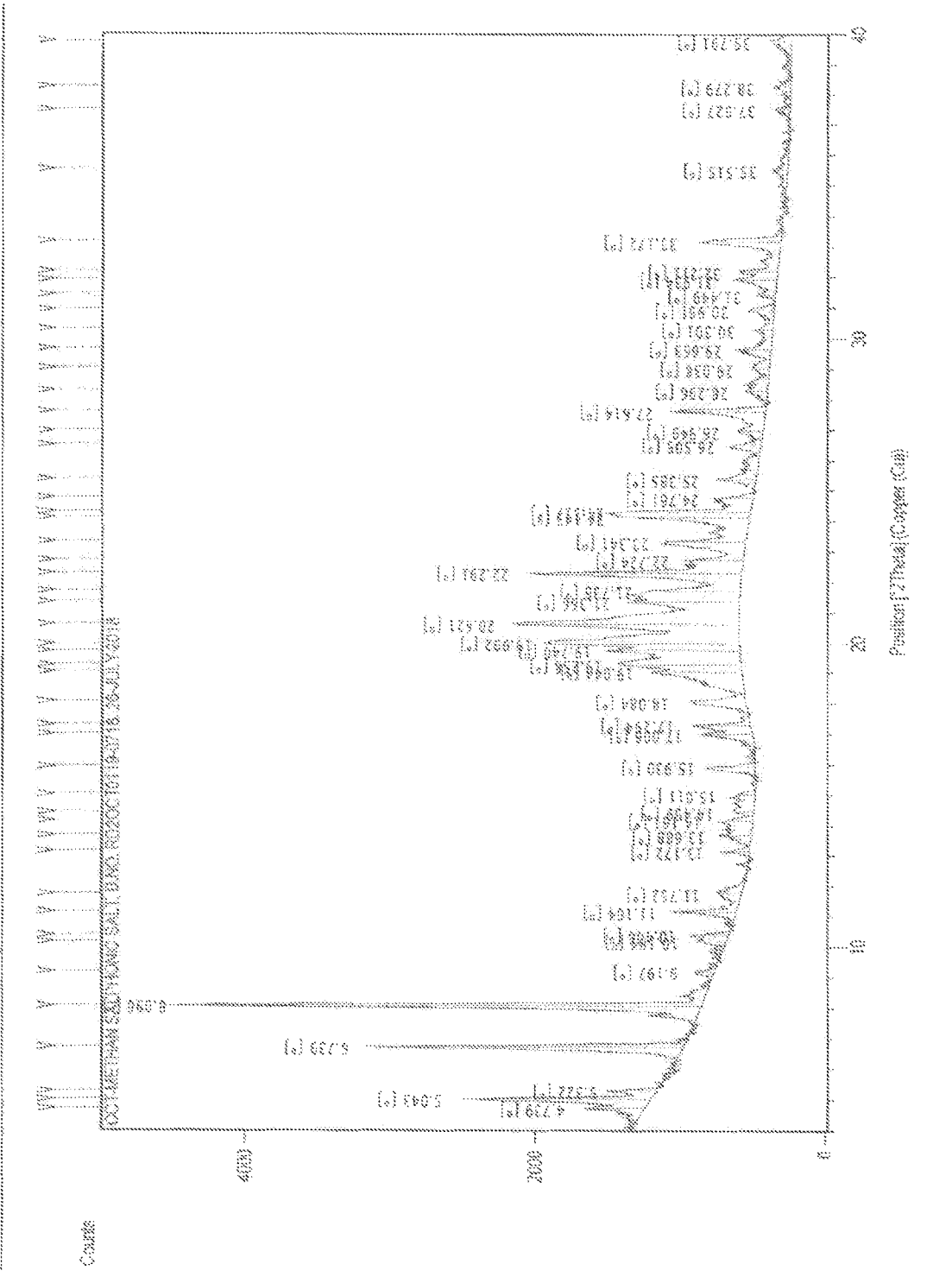

FIG. 29. The crystalline form of Octenidine methane sulfonic acid having crystalline form has an X-ray powder diffraction pattern.

Figure 30:
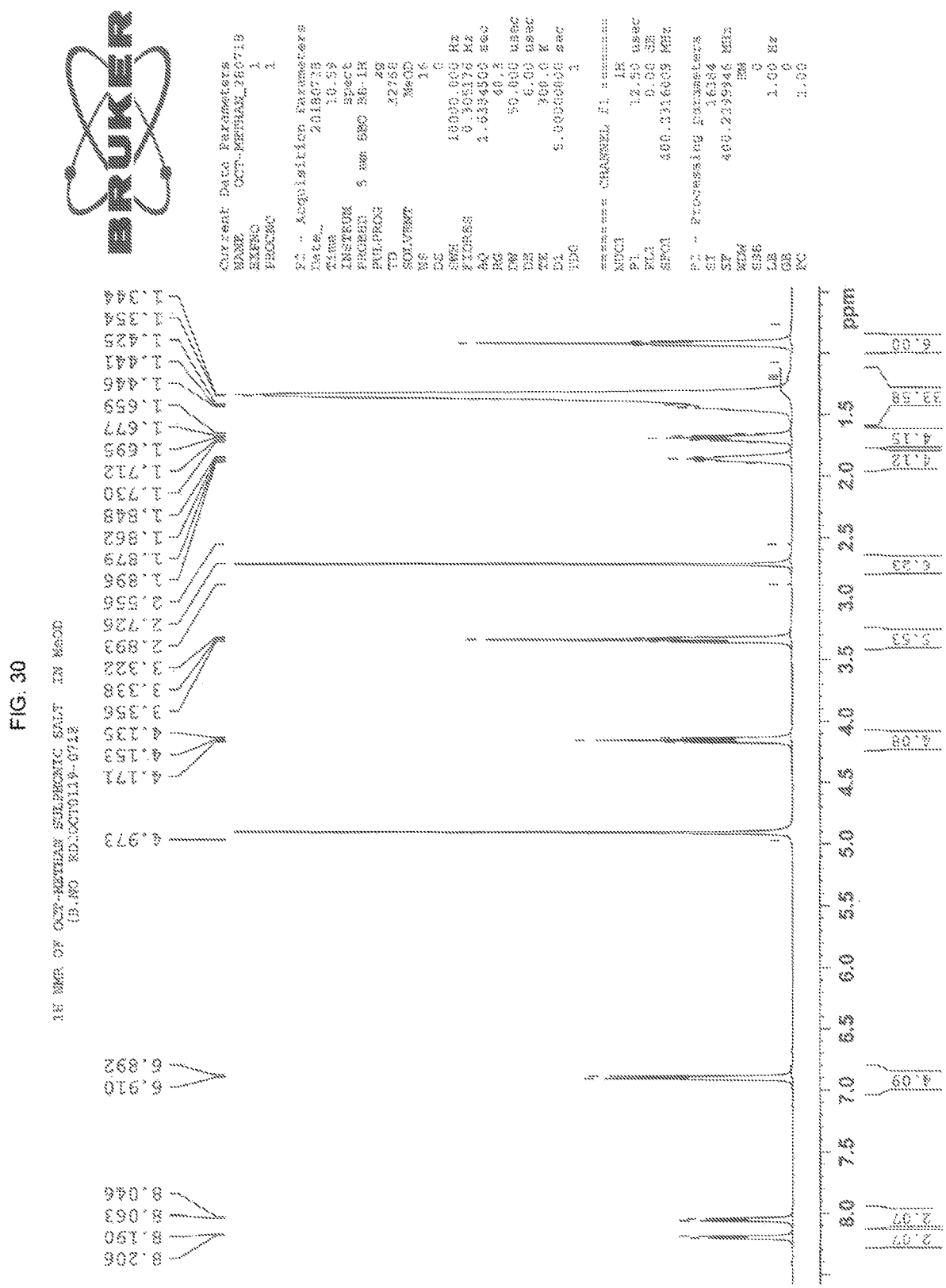

FIG. 30. The crystalline form of Octenidine methane sulfonic acid salt having Nuclear Magnetic Resonance.

Figure 31:
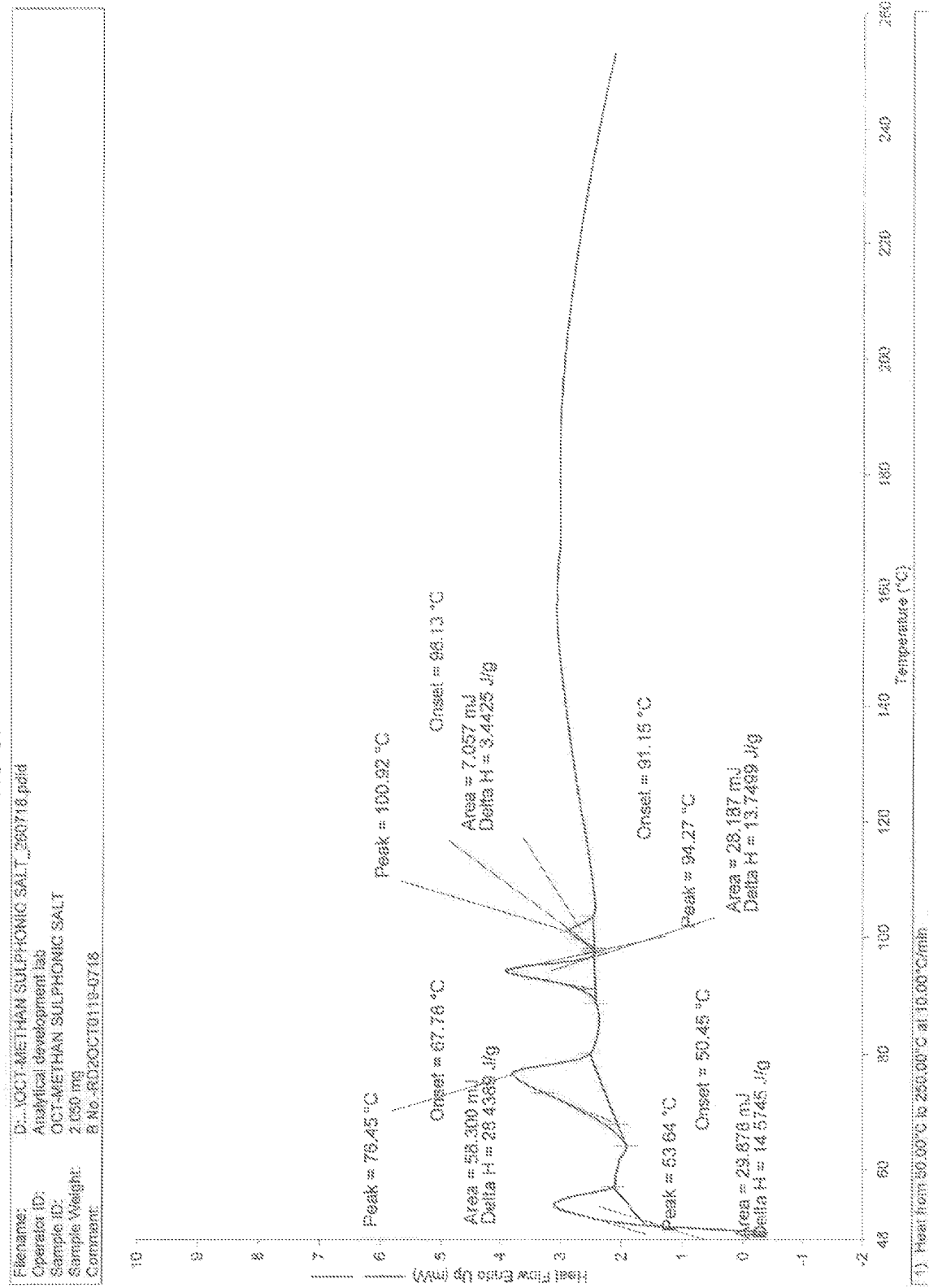

FIG. 31. The crystalline form of Octenidine methane sulfonic acid having a differential scanning calorimetry analysis.

Figure 32:
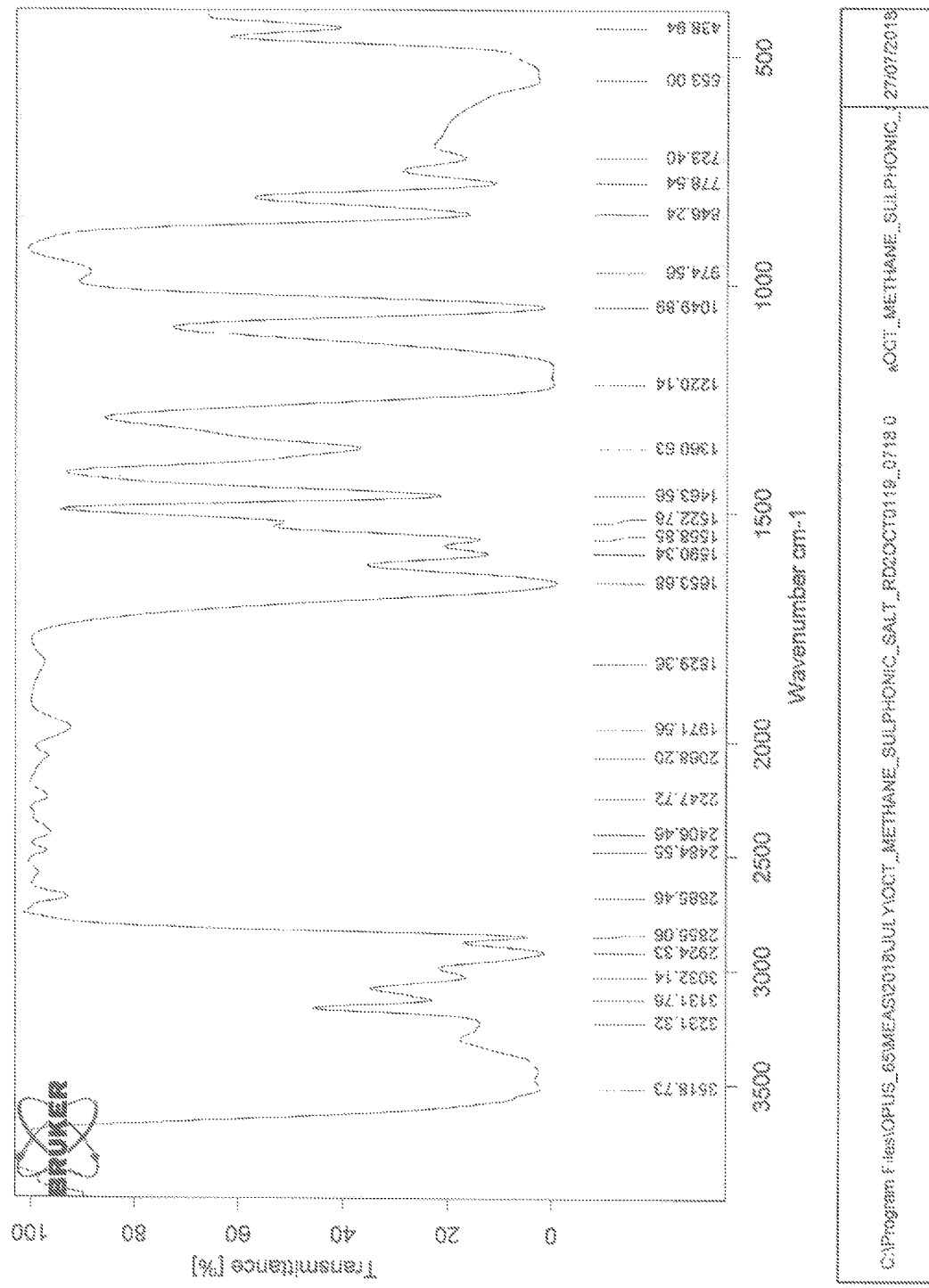

FIG. 32. The crystalline form of Octenidine methane sulfonic acid having a infrared absorption spectrum analysis.

DETAILED DESCRIPTION OF THE INVENTION

The present invention provides novel forms of the Octenidine based compounds, particularly novel crystalline form of the Octenidine acid addition salts. The novel crystalline form of the Octenidine based compounds is benzoate, acetate, gluconate, peracetate, perchloroacetate, laureate, palmitate, methane sulfonic acid salt.

Yet another object of the present invention is to provide a process for the preparation of novel crystalline form of the Octenidine based compounds.

In particular, the novel crystalline forms Octenidine are compounds of formula (A), formula (B) and formula (C) as represented below.

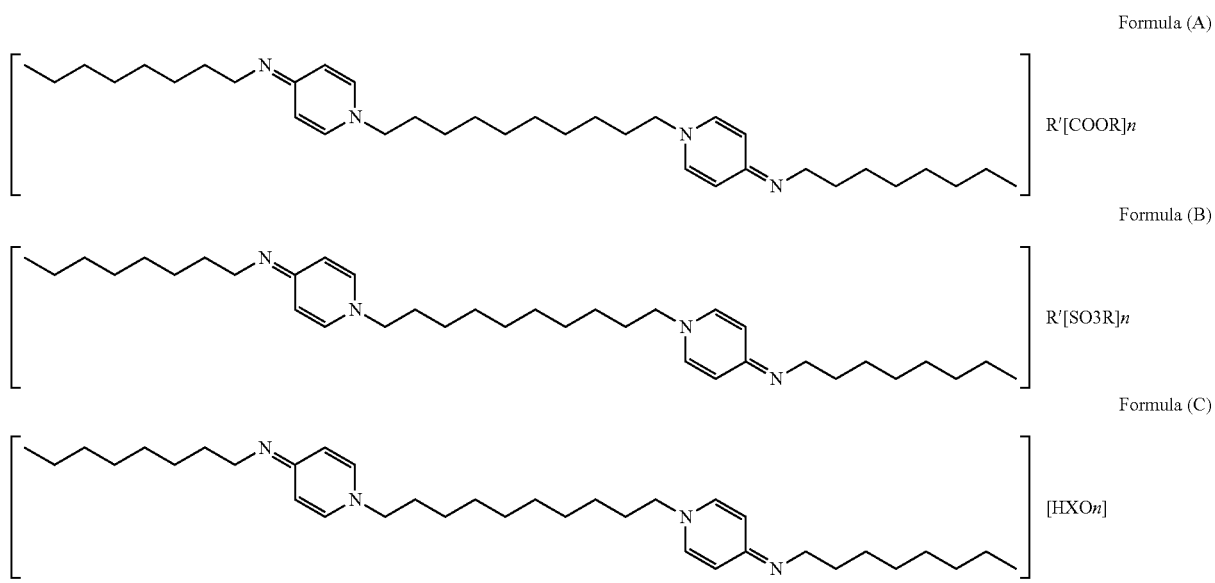

where in, n=1, 2, 3, 4 and R'=un-substituted or substituted aryl or alkyl group; R is hydroxy or hydrogen, X is chlorine, bromine and iodine.

wherein, n=1 and R'=un-substituted or substituted aryl or alkyl group; and n=2 and R'=un-substituted or substituted alkyl or aryl group.

wherein, n=1 and R'=un-substituted or substituted aryl or alkyl group; i.e. benzoic acid, salicylic acid, p-methyl benzoic acid, acetate, peracetic acid, laureate, palmitate etc. and n=2 and R'=un-substituted or substituted alkyl or aryl group. i. e oxalic acid, malonic acid, succinic acid, tartaric acid, gluconate etc.

wherein, n=1 and R'=un-substituted or substituted aryl or alkyl group; R=H; i.e. methane sulfonic acid, ethane sulfonic acid, propane sulfonic acid, benzene sulfonic acid, p-toluene sulfonic acid etc.

wherein, n=1, 2, 3, 4, hypohalous acid (HXO), halous acid $(HXO_2)$ halic acid $(HXO_3)$ and perhalic acid $(HXO_4)$ n=4 and X═Cl, Br, I, i.e. HClO, HClO$_2$, HClO$_3$, HClO$_4$, HBrO, HBrO$_3$, HBrO$_4$, HIO, HIO$_3$, HIO$_4$.

The present invention provides a process of preparation of crystalline Octenidine based compounds of formula (A), which comprises
(a) treating with Octenidine with suitable organic acid in a solvent;
(b) isolating the product as a salt with organic acid from an organic solvent; optionally stage (c)
(c) purifying the salt from organic solvent.

Organic acid may be selected from benzoic acid, salicylic acid, p-methyl benzoic acid, acetate, oxalic acid, malonic acid, succinic acid, tartaric acid, gluconate, laureate, palmitate etc.

The present invention further provides a process of preparation of crystalline Octenidine based compounds of formula (B), which comprises
(a) treating with Octenidine with sulfonic acid in a solvent;
(b) isolating the product as a salt with organic acid from an organic solvent; optionally stage (c)
(c) purifying the salt from organic solvent.

Sulfonic acid may be selected from methane sulfonic acid, ethane sulfonic acid, propane sulfonic acid, benzene sulfonic acid, p-toluene sulfonic acid.

The present invention further provides a process of preparation of crystalline Octenidine based compounds of formula (C), which comprises
(a) treating with Octenidine with per halogenate acid in a solvent;
(b) isolating the product as a salt with organic acid from an organic solvent;
(c) purifying the salt from organic solvent.

Per halogenate acid may be selected from HClO, HClO$_2$, HClO$_3$, HClO$_4$, HBrO, HBrO$_3$, HBrO$_4$, HIO, HIO$_3$, HIO$_4$.

The solvent used in Step a) can be selected from branched or liner $C_1$-$C_4$ of alcohols, ketones, esters, nitriles or halogenated solvents or aromatic hydrocarbons.

The solvent used in Step c) can be selected from branched or liner $C_1$-$C_4$ of alcohols, ketones, esters, nitriles or halogenated solvents or aromatic hydrocarbons.

Octenidine based compounds, organic acids customarily used for forming pharmaceutically acceptable acid addition salts include, by way of example and not limitation, acetic acid, 2,2-dichloroacetic acid, adipic acid, ascorbic acid (D- or L-form thereof, especially the L-form thereof), aspartic acid (D- or L-form thereof, especially the L-form thereof), benzenesulfonic acid, benzoic acid, 4-acetamido-benzoic acid, camphoric acid ((+)- or (−)-form thereof, especially the (+)-form thereof), camphor-10-sulfonic acid ((+)- or (−)-form thereof, especially the (+)-form thereof), capric acid (decanoic acid), caproic acid (hexanoic acid), caprylic acid (octanoic acid), carbonic acid, cinnamic acid, citric acid, cyclamic acid, dodecylsulfuric acid, ethane-1,2-disulfonic acid, ethane sulfonic acid, 2-hydroxy-ethane sulfonic acid, formic acid, fumaric acid, galactaric acid, gentisic acid, glucoheptonic acid (D- or L-form thereof, especially the D-form thereof), gluconic acid (D- or L-form thereof, especially the D-form thereof); glucuronic acid (D- or L-form thereof, especially the D-form thereof), glutamic acid, glutaric acid, 2-oxo-glutaric acid, glycerophosphoric acid, glycolic acid, hippuric acid, isobutyric acid, lactic acid (D- or L-form thereof), lactobionic acid, lauric acid, maleic acid, malic acid (D- or L-form thereof), malonic acid, mandelic acid (D- or L-form thereof), methane sulfonic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid (embonic acid), propionic acid, pyroglutamic acid (D- or L-form thereof, especially the L-form thereof), salicyclic acid, 4-aminosalicyclic acid, sebacic acid, stearic acid, succinic acid, tartaric acid (D- or L-form thereof), thiocyanic acid, toluenesulfonic acid (especially the p-isomer thereof), undecylenic acid, and the like.

In an embodiment, the present invention further provides a crystalline form of Octenidine benzoate salt. The crystalline form of Octenidine benzoate salt can be characterized by having X-ray powder diffraction pattern with peaks at 4.75, 5.80, 6.30, 11.61, 12.59, 14.29, 15.10, 15.83, 17.64, 18.91, 19.39, 19.97, 21.16, 21.83, 22.40, 23.10, 23.54, 24.29, 25.39, 26.42, 27.12, 28.92, 30.40, 31.65, 32.89, 33.33, 35.88, 36.69, 38.03 and 39.58±0.2° 2θ.

The crystalline form of Octenidine benzoate salt can be also characterized by DSC two endothermic pecks observed peck is 109.31° C., 128.95° C.

In an embodiment, the present invention further provides a crystalline form of Octenidine acetate salt. The crystalline form of Octenidine acetate salt can be characterized by having X-ray powder diffraction pattern with peaks at 5.08, 7.68, 9.02, 10.02, 11.12, 12.30, 14.07, 14.92, 15.98, 17.02, 17.95, 19.77, 20.32, 20.83, 22.26, 22.77, 23.37, 24.14, 24.84, 25.52, 26.99, 27.32, 31.09, 32.43, 34.38 and 36.23±0.2° 2θ.

The crystalline form of Octenidine acetate salt can be also characterized by DSC one endothermic peck observed peck is 203.56° C.

In an embodiment, the present invention further provides a crystalline form of Octenidine gluconate salt. The crystalline form of Octenidine gluconate salt can be characterized by having X-ray powder diffraction pattern with peaks at 5.46, 10.70, 13.25, 14.89, 16.37, 19.32, 19.82, 20.58, 21.79, 23.26, 25.81, 26.32, 26.81, 30.00, 31.41, 32.09, 34.27, 35.56, 36.80, 38.11, 38.72 and 39.26±0.2° 2θ.

The crystalline form of Octenidine gluconate salt can be also characterized by DSC two endothermic pecks observed peck is 87.46° C., 206.97° C.

In an embodiment, the present invention further provides a crystalline form of Octenidine per acetic acid salt. The crystalline form of Octenidine per acetic acid salt can be characterized by having X-ray powder diffraction pattern with peaks at 4.70, 6.32, 7.70, 8.51, 9.19, 10.15, 10.35, 11.45, 11.70, 12.74, 13.59, 14.07, 14.70, 15.37, 15.88, 16.25, 16.97, 17.28, 17.98, 18.99, 19.69, 19.99, 20.94, 22.53, 23.30, 23.62, 23.99, 24.74, 25.08, 25.99, 26.39, 26.87, 27.36, 28.16, 29.72, 31.68, 32.59, 33.05, 33.65, 35.54, 36.58, 37.14, and 37.57±0.2° 2θ.

The crystalline form of Octenidine per acetic acid salt can be also characterized by DSC two endothermic pecks observed peck is 58.92° C., 202.28° C.

In an embodiment, the present invention further provides a crystalline form of Octenidine perchloric acid salt. The crystalline form of Octenidine perchloric acid salt can be characterized by having X-ray powder diffraction pattern with peaks at 5.25, 10.49, 12.80, 13.66, 14.54, 14.88, 15.18, 15.79, 16.87, 17.87, 18.35, 18.86, 19.18, 20.74, 21.50, 22.67, 23.09, 23.47, 25.34, 25.64, 26.60, 26.87, 28.99, 31.09, 31.68, 32.56, 34.87, 36.19, 36.86, and 39.10±0.2° 2θ.

The crystalline form of Octenidine perchloric acid salt can be also characterized by DSC one endothermic peck observed peck is 135.03° C.

In an embodiment, the present invention further provides a crystalline form of Octenidine lauric acid salt. The crystalline form of Octenidine lauric acid salt can be characterized by having X-ray powder diffraction pattern with peaks at 4.30, 5.92, 9.86, 10.06, 10.16, 10.74, 11.69, 12.63, 13.90, 15.60, 16.93, 17.74, 18.49, 19.11, 19.61, 20.06, 20.50, 21.00, 21.22, 21.68, 21.98, 22.83, 23.85, 23.99, 24.57, 24.98, 25.36, 26.25, 26.98, 27.53, 28.18, 29.02, 29.43, 30.15, 31.99, 35.39, 36.54, 37.50, 38.56 and 39.51±0.2° 2θ.

The crystalline form of Octenidine Lauric acid salt can be also characterized by DSC one endothermic peck observed peck is 137.63° C.

In an embodiment, the present invention further provides a crystalline form of Octenidine palmitic acid salt. The crystalline form of Octenidine palmitic acid salt can be characterized by having X-ray powder diffraction pattern with peaks at 4.42, 5.03, 5.41, 5.84, 5.92, 6.59, 7.80, 9.72, 9.81, 10.11, 10.78, 10.95, 12.16, 13.62, 14.91, 15.60, 17.47, 19.05, 19.52, 20.12, 20.36, 20.48, 21.40, 22.22, 22.74, 23.82, 24.64, 25.74, 26.47, 27.41, 28.70, 30.11, 31.81, 33.76, 35.23, 37.20, 38.65 and 39.06±0.2° 2θ.

The crystalline form of Octenidine palmitic acid salt can be also characterized by DSC one endothermic peck observed peck is 77.58 and 102.74° C.

In an embodiment, the present invention further provides a crystalline form of Octenidine methane sulfonic acid salt. The crystalline form of Octenidine methane sulfonic acid salt can be characterized by having X-ray powder diffraction pattern with peaks at 4.74, 5.04, 5.32, 6.74, 8.10, 9.20, 10.18, 10.41, 11.16, 11.7513.17, 13.69, 14.16, 14.46, 15.01, 15.93, 17.01, 17.29, 18.08, 19.04, 19.26, 19.74, 19.99, 20.62, 21.37, 21.74, 22.29, 22.72, 23.34, 24.14, 24.32, 24.76, 25.39, 26.51, 26.95, 27.61, 28.29, 29.04, 29.66, 30.30, 30.95, 31.45, 31.93, 32.21, 33.17, 35.51, 37.53, 38.28, and 39.79±0.2° 2θ.

The crystalline form of Octenidine methane sulfonic acid salt can be also characterized by DSC one endothermic peck observed peck is 102.45° C.

The present invention provides a process of preparation of crystalline Octenidine based compounds of formula (A), which comprises
(a) treating Octenidine with suitable organic acid in a solvent system;
(b) isolating the product as a salt with organic acid from an organic solvent; optionally stage (c)
(c) purifying the salt from organic solvent.

Suitable organic acid may be selected from benzoic acid, salicylic acid, p-methyl benzoic acid, acetate, oxalic acid, malonic acid, succinic acid, tartaric acid, gluconate, laureate, palmitate etc.

The process for preparing crystalline form of Octenidine benzoate salt or acetate salt or gluconate salt or laureate salt or palmitate salt, which comprises treating Octenidine with benzoic acid or acetic acid or gluconic acid or Lauric acid or palmitic acid in suitable solvent.

The solvent system is preferably selected so as to facilitate the salt reaction and to allow subsequent separation of the resulting Octenidine benzoate salt or acetate salt or gluconate salt or laureate salt or palmitate salt. Advantageously, both Octenidine and the benzoic acid or acetic acid or gluconic acid or Lauric acid or palmitic acid are dissolvable, at least partly, in the solvent system, at least at elevated temperatures. In the process, a mixture, slurry, or solution of Octenidine and a solvent may be contacted with a benzoic acid or acetic acid or gluconic acid or Lauric acid or palmitic acid, or conversely, a mixture, slurry, or solution of benzoic acid or acetic acid or gluconic acid or Lauric acid or palmitic acid and a solvent may be contacted with Octenidine. In another embodiment, the Octenidine and organic acid may be combined with a solvent system separately prior to being contacted together, whereby the solvent system used for benzoic acid or acetic acid or gluconic acid or Lauric acid or palmitic acid may be identical with or different from the solvent system used for the Octenidine. The solvent system can be a single solvent or a mixture of solvents. When two or more solvents are used, a two phase reaction scheme may be used wherein the Octenidine and benzoic acid or acetic acid or gluconic acid or Lauric acid or palmitic acid are primarily reacted in one phase and the resulting Octenidine benzoate salt or acetate salt or gluconate salt or laureate salt or palmitate salt compound is primarily present in the other phase due to, inter alia, solubility differences, etc. Suitable solvents include a lower alcohol (C1-C4) such as methanol, ethanol, isopropanol, n-propanol, n-butanol, iso-butanol, tert-butanol; ester such as ethyl acetate, isopropyl acetate, butyl acetate, iso-butyl acetate; ketone such as acetone, methyl ethyl ketone, methyl tert-butyl ketone; ether such as tetrahydrofuran, di ethyl ether, di isopropyl ether, dioxane and the like.

The temperature of contact of Octenidine and benzoic acid or acetic acid or gluconic acid or Lauric acid or palmitic acid in the solvent system is from ambient to the boiling point of the solvent system, with elevated temperatures, but generally less than the boiling point, being preferred. It is not required that a complete solution is formed in this step, i.e. a slurry or two-phase solution are also possible, though a single solution is generally preferred.

The Octenidine benzoate salt or acetate salt or gluconate salt or laureate salt or palmitate salt compound can be isolated or recovered from the salt forming reaction by any convenient means. For example, the Octenidine benzoate salt or acetate salt or gluconate salt or laureate salt or palmitate salt compound can be precipitated out of a solution or reaction mixture. The precipitation may be spontaneous depending upon the solvent system used and the conditions. Alternatively, the precipitation can be induced by reducing the temperature of the solvent, especially if the initial temperature of contact is elevated. The precipitation may, also be facilitated by reducing the volume of the solution/solvent or by adding a contra solvent, i.e. a liquid miscible with the solvent in which the Octenidine benzoate salt or acetate salt or gluconate salt or laureate salt or palmitate salt is less soluble. Seed crystals of Octenidine benzoate may also be added to help induce precipitation. The precipitated Octenidine benzoate salt or acetate salt or gluconate salt or laureate salt or palmitate salt compound can be isolated by conventional methods such as filtration or centrifugation, optionally washed and dried, preferably under diminished pressure.

In the preferred embodiment, Octenidine (I) is dissolved in methanol and treated with benzoic acid to obtain Octenidine benzoate.

The crystalline form of Octenidine benzoate salt can be characterized by having X-ray powder diffraction pattern with peaks at 4.75, 5.80, 6.30, 11.61, 12.59, 14.29, 15.10, 15.83, 17.64, 18.91, 19.39, 19.97, 21.16, 21.83, 22.40, 23.10, 23.54, 24.29, 25.39, 26.42, 27.12, 28.92, 30.40, 31.65, 32.89, 33.33, 35.88, 36.69, 38.03 and 39.58±0.2° 2θ.

The crystalline form of Octenidine benzoate having Nuclear Magnetic Resonance in FIG. 2. The crystalline form of Octenidine benzoate salt having a differential scanning calorimetry analysis in FIG. 3.

The crystalline form of Octenidine benzoate salt having a infrared absorption spectrum analysis in FIG. 4.

In an embodiment Octenidine (I) is dissolved in methanol and treated with acetic acid to obtain Octenidine acetate.

The crystalline form of Octenidine acetate salt can be characterized by having X-ray powder diffraction pattern with peaks at 5.08, 7.68, 9.02, 10.02, 11.12, 12.30, 14.07, 14.92, 15.98, 17.02, 17.95, 19.77, 20.32, 20.83, 22.26, 22.77, 23.37, 24.14, 24.84, 25.52, 26.99, 27.32, 31.09, 32.43, 34.38 and 36.23±0.2° 2θ.

The crystalline form of Octenidine acetate having crystalline form has an X-ray powder diffraction pattern substantially as depicted in FIG. 5

The crystalline form of Octenidine acetate having crystalline form has Nuclear Magnetic Resonance in FIG. 6.

The crystalline form of Octenidine acetate having a differential scanning calorimetry analysis in FIG. 7

The crystalline form of Octenidine acetate having a infrared absorption spectrum analysis in FIG. 8

In the embodiment, Octenidine (I) is dissolved in methanol and treated with gluconic acid to obtain Octenidine gluconate. The crystalline form of Octenidine gluconate salt can be characterized by having X-ray powder diffraction pattern with peaks at 5.46, 10.70, 13.25, 14.89, 16.37, 19.32, 19.82, 20.58, 21.79, 23.26, 25.81, 26.32, 26.81, 30.00, 31.41, 32.09, 34.27, 35.56, 36.80, 38.11, 38.72 and 39.26±0.2° 2θ.

The crystalline form of Octenidine gluconate having crystalline form has an X-ray powder diffraction pattern substantially as depicted in FIG. 9

The crystalline form of Octenidine gluconate having crystalline form has Nuclear Magnetic Resonance in FIG. 10.

The crystalline form of Octenidine gluconate having a differential scanning calorimetry analysis in FIG. 11.

The crystalline form of Octenidine gluconate having a infrared absorption spectrum analysis in FIG. 12.

The present invention further provides a crystalline form of Octenidine lauric acid salt. The crystalline form of Octenidine lauric acid salt can be characterized by having X-ray powder diffraction pattern with peaks at 4.30, 5.92, 9.86, 10.06, 10.16, 10.74, 11.69, 12.63, 13.90, 15.60, 16.93, 17.74, 18.49, 19.11, 19.61, 20.06, 20.50, 21.00, 21.22, 21.68, 21.98, 22.83, 23.85, 23.99, 24.57, 24.98, 25.36, 26.25, 26.98, 27.53, 28.18, 29.02, 29.43, 30.15, 31.99, 35.39, 36.54, 37.50, 38.56 and 39.51±0.2° 2θ.

The crystalline form of Octenidine Lauric acid salt can be also characterized by DSC one endothermic peck observed peck is 137.63° C.

The crystalline form of Octenidine lauric acid having crystalline form has an X-ray powder diffraction pattern as depicted in FIG. 21.

The crystalline form of Octenidine lauric acid salt having Nuclear Magnetic Resonance in FIG. 22.

The crystalline form of Octenidine lauric acid having a differential scanning calorimetry analysis in FIG. 23.

The crystalline form of Octenidine lauric acid having a infrared absorption spectrum analysis in FIG. 24.

The present invention further provides a crystalline form of Octenidine palmitic acid salt. The crystalline form of Octenidine palmitic acid salt can be characterized by having X-ray powder diffraction pattern with peaks at 4.42, 5.03, 5.41, 5.84, 5.92, 6.59, 7.80, 9.72, 9.81, 10.11, 10.78, 10.95, 12.16, 13.62, 14.91, 15.60, 17.47, 19.05, 19.52, 20.12, 20.36, 20.48, 21.40, 22.22, 22.74, 23.82, 24.64, 25.74, 26.47, 27.41, 28.70, 30.11, 31.81, 33.76, 35.23, 37.20, 38.65 and 39.06±0.2° 2θ.

The crystalline form of Octenidine palmitic acid salt can be also characterized by DSC one endothermic peck observed peck is 77.58 and 102.74° C.

The crystalline form of Octenidine palmitic acid having crystalline form has an X-ray powder diffraction pattern as depicted in FIG. 25.

The crystalline form of Octenidine palmitic acid salt having Nuclear Magnetic Resonance in FIG. 26.

The crystalline form of Octenidine palmitic acid having a differential scanning calorimetry analysis in FIG. 27.

The crystalline form of Octenidine palmitic acid having a infrared absorption spectrum analysis in FIG. 28.

The present invention further provides a process of preparation of crystalline Octenidine based compounds of formula (B), which comprises
(a) treating with Octenidine with sulfonic acid in a solvent system;
(b) isolating the product as a salt with organic acid from an organic solvent; optionally stage (c)
(c) purifying the salt from organic solvent.

Sulfonic acid may be selected from methane sulfonic acid, ethane sulfonic acid, propane sulfonic acid, benzene sulfonic acid, p-toluene sulfonic acid.

The present invention also provides a process for preparing crystalline form of Octenidine methane sulfonic acid salt, which comprises treating Octenidine with methane sulfonic acid in suitable solvent.

The solvent system is preferably selected so as to facilitate the salt reaction and to allow subsequent separation of the resulting Octenidine methane sulfonic acid salt. Advantageously, both Octenidine and the methane sulfonic acid are dissolvable, at least partly, in the solvent system, at least at elevated temperatures. In the process, a mixture, slurry, or solution of Octenidine and a solvent may be contacted with a benzoic acid, or conversely, a mixture, slurry, or solution of methane sulfonic acid and a solvent may be contacted with Octenidine. In another embodiment, both Octenidine and methane sulfonic acid may be combined with a solvent system separately prior to being contacted together, whereby the solvent system used for methane sulfonic acid may be identical with or different from the solvent system used for the Octenidine. The solvent system can be comprised of a single solvent or a mixture of solvents. When two or more solvents are used, a two phase reaction scheme may be used wherein the Octenidine and methane sulfonic acid are primarily reacted in one phase and the resulting Octenidine mean sulfonic acid salt compound is primarily present in the other phase due to, inter alia, solubility differences, etc. Suitable solvents include a lower alcohol (C1-C4) such as methanol, ethanol, isopropanol, n-propanol, n-butanol, iso-butanol, tert-butanol; ester such as ethyl acetate, isopropyl acetate, butyl acetate, iso-butyl acetate; ketone such as acetone, methyl ethyl ketone, methyl tert-butyl ketone; ether such as tetrahydrofuran, di ethyl ether, di isopropyl ether, dioxane and the like.

The temperature of contact of Octenidine and methane sulfonic acid in the solvent system is from ambient to the boiling point of the solvent system, with elevated temperatures, but generally less than the boiling point, being preferred. It is not required that a complete solution is formed in this step, i.e. a slurry or two-phase solution are also possible, though a single solution is generally preferred.

The Octenidine methane sulfonic salt compound can be isolated or recovered from the salt forming reaction by any convenient means. In an embodiment, the Octenidine methane sulfonic salt compound can be precipitated out of a solution or reaction mixture. The precipitation may be spontaneous depending upon the solvent system used and the conditions. Alternatively, the precipitation can be induced by reducing the temperature of the solvent, especially if the initial temperature of contact is elevated. The precipitation may also be facilitated by reducing the volume of the solution/solvent or by adding a contra solvent, i.e. a liquid miscible with the solvent in which the Octenidine methane sulfonic salt is less soluble. Seed crystals of Octenidine methane sulfonic may also be added to help induce precipitation. The precipitated Octenidine methane sulfonic salt compound can be isolated by conventional methods such as filtration or centrifugation, optionally washed and dried, preferably under diminished pressure.

In the preferred embodiment, Octenidine (I) is dissolved in methanol and treated with methane sulfonic acid to obtain Octenidine methane sulfonic salt.

The crystalline form of Octenidine methane sulfonic acid salt can be characterized by having X-ray powder diffraction pattern with peaks at 4.74, 5.04, 5.32, 6.74, 8.10, 9.20, 10.18, 10.41, 11.16, 11.7513.17, 13.69, 14.16, 14.46, 15.01, 15.93, 17.01, 17.29, 18.08, 19.04, 19.26, 19.74, 19.99, 20.62, 21.37, 21.74, 22.29, 22.72, 23.34, 24.14, 24.32, 24.76, 25.39, 26.51, 26.95, 27.61, 28.29, 29.04, 29.66, 30.30, 30.95, 31.45, 31.93, 32.21, 33.17, 35.51, 37.53, 38.28, and 39.79±0.2° 2θ.

The crystalline form of Octenidine methane sulfonic acid salt can be also characterized by DSC one endothermic peck observed peck is 102.45° C.

The crystalline form of Octenidine methane sulfonic acid having crystalline form has an X-ray powder diffraction pattern as depicted in FIG. 29

The crystalline form of Octenidine methane sulfonic acid salt having Nuclear Magnetic Resonance in FIG. 30.

The crystalline form of Octenidine methane sulfonic acid having a differential scanning calorimetry analysis in FIG. 31.

The crystalline form of Octenidine methane sulfonic acid having a infrared absorption spectrum analysis in FIG. 32.

The present invention further provides a process of preparation of crystalline Octenidine based compounds of formula (C), which comprises
(a) treating with Octenidine with per halogenate acid in a solvent;
(b) isolating the product as a salt with organic acid from an organic solvent;
(c) purifying the salt from organic solvent.

Per halogenate acid may be selected from $HClO$, $HClO_2$, $HClO_3$, $HClO_4$, $HBrO$, $HBrO_3$, $HBrO_4$, $HIO$, $HIO_3$, $HIO_4$.

The present invention also provides a process for preparing crystalline form of Octenidine per acetic acid salt or perchloric acid salt, which comprises treating Octenidine with peracetic acid or perchloric acid in suitable solvent.

The reaction is preferably carried out in suitable solvent. The solvent system is preferably selected so as to facilitate the salt reaction and to allow subsequent separation of the resulting peracetate. Advantageously, both Octenidine and peracetic acid or perchloric acid are dissolvable, at least partly, in the solvent system, at least at elevated temperatures. In the process, a mixture, slurry, or solution of Octenidine and a solvent may be contacted with a peracetic acid or perchloric acid, or conversely, a mixture, slurry, or solution of peracetic acid or perchloric acid and a solvent may be contacted with Octenidine. In another embodiment, Octenidine and peracetic acid or perchloric acid partners may be combined with a solvent system separately prior to being contacted together, whereby the solvent system used for peracetic acid or perchloric acid may be identical with or different from the solvent system used for the Octenidine. The solvent system can comprise a single solvent or a mixture of solvents. When two or more solvents are used, a two phase reaction scheme may be used wherein the Octenidine and peracetic acid or perchloric acid are primarily reacted in one phase and the resulting Octenidine per acetic acid salt or perchloric acid salt compound is primarily present in the other phase due to, inter alia, solubility differences, etc. Suitable solvents include a lower alcohol ($C_1$-$C_4$) such as methanol, ethanol, isopropanol, n-propanol, n-butanol, iso-butanol, tert-butanol; ester such as ethyl acetate, isopropyl acetate, butyl acetate, iso-butyl acetate; ketone such as acetone, methyl ethyl ketone, methyl tert-butyl ketone; ether such as tetrahydrofuran, di ethyl ether, di isopropyl ether, dioxane and the like.

The temperature of contact of Octenidine and peracetic acid or perchloric acid in the solvent system is from ambient to the boiling point of the solvent system, with elevated temperatures, but generally less than the boiling point, being preferred. It is not required that a complete solution is formed in this step, i.e. a slurry or two-phase solution are also possible, though a single solution is generally preferred.

The Octenidine per acetic acid salt or perchloric acid salt compound can be isolated or recovered from the salt forming reaction by any convenient means. In an embodiment, the Octenidine per acetic acid salt or perchloric acid salt compound can be precipitated out of a solution or reaction mixture. The precipitation may be spontaneous depending upon the solvent system used and the conditions. Alternatively, the precipitation can be induced by reducing the temperature of the solvent, especially if the initial temperature of contact is elevated. The precipitation may also be facilitated by reducing the volume of the solution/solvent or by adding a contra solvent, i.e. a liquid miscible with the solvent in which the Octenidine per acetic acid salt or perchloric acid salt is less soluble. Seed crystals of Octenidine per acetic acid salt or perchloric acid salt may also be added to help induce precipitation. The precipitated Octenidine per acetic acid salt or perchloric acid salt compound can be isolated by conventional methods such as filtration or centrifugation, optionally washed and dried, preferably under diminished pressure.

In the preferred embodiment, Octenidine (I) is dissolved in methanol and treated with per acetic acid to obtain Octenidine per acetic acid.

The crystalline form of Octenidine per acetic acid salt can be characterized by having X-ray powder diffraction pattern with peaks at 4.70, 6.32, 7.70, 8.51, 9.19, 10.15, 10.35, 11.45, 11.70, 12.74, 13.59, 14.07, 14.70, 15.37, 15.88, 16.25, 16.97, 17.28, 17.98, 18.99, 19.69, 19.99, 20.94, 22.53, 23.30, 23.62, 23.99, 24.74, 25.08, 25.99, 26.39, 26.87, 27.36, 28.16, 29.72, 31.68.32.59, 33.05, 33.65, 35.54, 36.58, 37.14, and 37.57±0.2° 2θ.

The crystalline form of Octenidine per acetic acid having crystalline form has an X-ray powder diffraction pattern substantially as depicted in FIG. 13

The crystalline form of Octenidine per acetic acid having Nuclear Magnetic Resonance in FIG. 14.

The crystalline form of Octenidine per acetic acid having a differential scanning calorimetry analysis in FIG. 15.

The crystalline form of Octenidine per acetic acid having a infrared absorption spectrum analysis in FIG. 16.

The present invention further provides a crystalline form of Octenidine perchloric salt The crystalline form of Octenidine perchloric salt can be characterized by having X-ray powder diffraction pattern with peaks at The crystalline form of Octenidine perchloric salt having X-ray powder diffraction pattern with peaks at 5.25, 10.49, 12.80, 13.66, 14.54, 14.88, 15.18, 15.79, 16.87, 17.87, 18.35, 18.86, 19.18, 20.74, 21.50, 22.67, 23.09, 23.47, 25.34, 25.64, 26.60, 26.87, 28.99, 31.09, 31.68, 32.56, 34.87, 36.19, 36.86, and 39.10±0.2° 2θ.

The crystalline form of Octenidine perchloric having crystalline form has an X-ray powder diffraction pattern substantially as depicted in FIG. 17

The crystalline form of Octenidine perchloric having Nuclear Magnetic Resonance in FIG. 18.

The crystalline form of Octenidine perchloric acid, having a differential scanning calorimetry analysis in FIG. 19

The crystalline form of Octenidine perchloric acid having a infrared absorption spectrum analysis in FIG. 20.

The present invention also provides a process for preparing crystalline form of Octenidine perchloric acid, which comprises treating Octenidine with perchloric acid in suitable solvent.

In the preferred embodiment, Octenidine (I) is dissolved in methanol and treated with perchloric acid to obtain Octenidine perchloric acid salt.

The present invention will be more fully understood from the following examples, which illustrates the present invention. It will be appreciated by persons skilled in the art that various modification of the invention may be possible without departing from the spirit and scope of the invention.

References U.S. Pat. No. 4,598,082
Example:1[AM1]

A. A mixture of 4-octylaminopyridine (10 g., 0.048 mole) and octyl bromide (8 ml., 0.048 mole) was heated at 125° C. for 8 hr. on one day and for 4 more hr. on the next day. The resulting solid was slurried, first in ether, then in ether-tetrahydrofuran (2:1) and finally in tetrahydrofuran, collected by filtration, washed with ether on the filter, and dried (70° C., 0.1 mm.) affording N-(1-octyl-4(1H)-pyridinylidene)octanamine monohydrobromide (11.95 g., 83% yield, m.r. 108°–112° C.), which is the monohydrobromide salt of the compound of Formula I wherein both R and R' are octyl.

B. A mixture of 4-octylaminopyridine (25 g., 0.121 mole) and octyl chloride (20.5 ml., 0.121 mole) was heated at 180° C. for 1 hr. More octyl chloride (0.5 ml.) was added and the mixture was again heated at 180° C. for 1 hr., then dissolved in dichloromethane. The dichloromethane solution was treated with charcoal, filtered, and stripped of solvent under vacuum. The solid residue was slurried in ether (1.5 kg.), collected by filtration, washed with ether (500 g.), isolated in a dry bag, and dried (50°–80° C., 0.1 mm.). The procedure was repeated using the same amounts of starting materials and the products were combined, affording N-(1-octyl-4 (1H)-pyridinylidene)octanamine monohydrochloride (80.5 g., 93% yield, m.r. 120°–125° C.), which is the monohydrochloride salt of the compound of Formula I wherein R and R' are both octyl.

C. Octyl chloride (800 ml., 4.70 mole) was added to a solution of 4-octylaminopyridine (650 g., 3.16 mole) in warm (50° C.) isooctane (b.p. 99.3° C.). The resulting solution was heated under reflux. Crystals began to separate from the solution after 2 hr. Refluxing was continued for 36 hr. The solution was then allowed to cool to room temperature and filtered. The solid was washed with cold cyclohexane (1 l.) then slurried in hot (70° C.) cyclohexane (4 l.) for 0.5 hr. The slurry was allowed to cool to 60° C. and filtered. The solid (1050 g.) was slurried in boiling cyclohexane for 0.5 hr. The slurry was cooled to 50° C. and filtered. The solid was dried at 60° C. under vacuum, affording N-(1-octyl-4(1H)-pyridinylidene)octanamine monohydrochloride (1035 g., 92% yield, m.r. 140°–142° C.), which is a higher melting crystalline form of the product of part B of this example.

D. A filtered solution of N-(1-octyl-4(1H)-pyridinylidene) octanamine monohydrochloride salt (33.5 g.) in methanol (335 ml.) was added dropwise with stirring to a filtered solution of saccharin sodium salt (20.1 g.) in water (2.5 l.). The mixture was stirred for several hours, allowed to stand overnight and filtered. The resulting solid was washed with water, and dried, first on the filter and then at 30°–35° C. under high vacuum using a dry ice condenser, affording N-(1-octyl-4(1H)-pyridinylidene)octanamine monosaccharin salt (42.2 g., m.r. 65°–67° C.).

Working Example 1

Process for Octenidine Benzoate Salt:

Octenidine free base (44 gm 0.079 mole) was dissolved in Methanol (110 ml) at ambient temperature. The reaction solution was cooled to 20° C. Slowly added Methanolic Benzoic acid (31.3 gm 0.256 moles) solution to get pH neutral to slight acidic Reaction mixture was stirred for 1 hr and the solvent was distilled off completely. The product was suspended in Ethyl acetate The product was dried at 45° C. under vacuum till LOD less than 2.0%. HPLC Purity: 94.67%; 1H NMR (DMSO) δ–1.25-1.73 (m, 40H), 3.24 (t, 4H), 4.08 (t, 4H), 6.86-7.05 (d, 4H), 8.08-8.27 (d, 4H); DSC Melting point=105-129° C. [two endothermic peaks observed peak is 109.31° C., 128.95° C.]; HPLC Assay: 76.30%, CHN analysis: C=75.06%, N=6.68%, H=9.57%; Loss on Drying=0.6%

Working Example 2

Process for Octenidine Acetate Salt:

Octenidine free base (44 gm 0.079 mole) was dissolved in Methanol (110 ml) at ambient temperature. The reaction solution was cooled to 20° C. Slowly added Acetic acid (14 gm 0.233 mole) to get pH neutral to slight acidic Reaction mixture was stirred for 1 hr and the solvent was distilled off completely. The product was suspended in Ethyl acetate. The product was dried at 45° C. under vacuum till LOD less than 2.0%. HPLC Purity: 99.85%; 1H NMR (DMSO) δ–1.25-1.73 (m, 40H), 3.24 (t, 4H), 4.08 (t, 4H), 6.86-7.05 (d, 4H), 8.08-8.27 (d, 4H), 10.99 (b, 2H), 1.60 (b, 6H) DSC Melting point=195-203° C.[One endothermic peak observed peak is 203.56° C.]; HPLC Assay: 83.50%, CHN analysis: C=66.23%, N=8.34%, H=10.88%; Loss on Drying=1.44%

Working Example 3

Process for Octenidine Gluconate Salt:

Octenidine free base (44 gm 0.079) was dissolved in Methanol (110 ml) at ambient temperature. The reaction solution was cooled to 20° C. Slowly added aqueous sol of Glucono delta lactone (46.2 gm 0.04 moles) to get pH neutral to slight acidic Reaction mixture was stirred for 1 hr and the solvent was distilled off completely. The product was suspended in Ethyl acetate. The product was dried at 45° C. under vacuum till LOD less than 2.0%. HPLC Purity: 99.67%; 1H NMR (DMSO) δ–1.25-1.73 (m, 40H), 3.24 (t, 4H), 4.11 (t, 4H), 3.76, 3.57, 3.42, 3.48, 4.64 (22H) 6.92 (m, 4H), 8.11-8.31 (d, 4H); DSC Melting point=74°–206° C.[two endothermic peaks observed peak is 87.46° C., 206.97° C.]; HPLC Assay: 78.97%, CHN analysis: C=57.54%, N=5.56%, H=9.86%; Loss on Drying=1.12%

Working Example 4

Process for Octenidine Per Acetic Acid Salt

Octenidine free base (44 gm, 0.079 moles) was dissolved in Methanol (110 ml) at ambient temperature. The reaction solution was cooled to 20° C. Slowly added Perchloric acid (16 gm 0.159 moles) to get pH neutral to slight acidic Reaction mixture was stirred for 1 hr. Filter the product and wash with Methanol. The product was dried at 45° C. under vacuum. Yield: 61.5%

DSC two endothermic peaks observed peak is 58.92° C., 202.28° C.

Working Example 5

Process for Octenidine Per Chloric Acid Salt:

Octenidine free base (44 gm 0.079 mole) was dissolved in Methanol (110 ml) at ambient temperature. The reaction solution was cooled to 20° C. Slowly added Per chloric acid (13.8 gm, 0.189 moles) to get pH neutral to slight acidic Reaction mixture was stirred for 1 hr and the solvent was distilled off completely. The product was suspended in acetone. The product was dried at 45° C. under vacuum. Yield: 27.9% DSC one endothermic peak observed peak is 135.03° C.

Working Example 6

Process for Octenidine Lauric Acid Salt:

Octenidine (44 gm 0.079 mole) was dissolve in Methanol (110 ml) at ambient temperature and added Lauric acid solution (38.3 gm 0.191 moles) Reaction mixture was stirred for 1 hr and the solvent was distilled off completely. The product was suspended in Acetone and filtered. The product was dried at 45° C. under vacuum. Yield: 51%, DSC Melting point=137.63° C., HPLC purity: 99.79%; HPLC Assay: 90.27%, CHN analysis: C=74.4%, N=5.52%, H=12.26%; Loss of Drying=4.0%

Working Example 7

Process for Octenidine Methane Sulfonic Acid Salt:

Octenidine (44 gm 0.079 mole) was dissolve in Methanol (110 ml) at ambient temperature and added Methane sulfonic acid (8.75 gm 0.09 moles) Reaction mixture was stirred for 1 hr and the solvent was distilled off completely. The product was suspended in Acetone and filtered. The product was dried at 45° C. under vacuum. Yield: 73.3%, DSC Melting point=102.45° C., HPLC purity: 99.5%; HPLC Assay: 92.56%, CHN analysis: C=60.6%, N=8.0%, H=8.65%, S=9.32%; Loss of Drying=4.13%

Working Example 8

Process for Octinidine Palmitic Acid Salt:

Octenidine free base (44 gm 0.079 mole) was dissolve in Methanol (110 ml) at ambient temperature and added Palmitic acid solution (44 gm 0.17 moles). The reaction mixture was stirred for 1 hr and filtered. The product was dried at 45° C. under vacuum. Yield: 40%. HPLC purity: 96.39%; CHN analysis: C=75.29%, N=4.30%, H=11.80%, S=9.32%; Loss of Drying=4.4%

The invention claimed is:

1. A crystalline compound of Formula A, B, or C

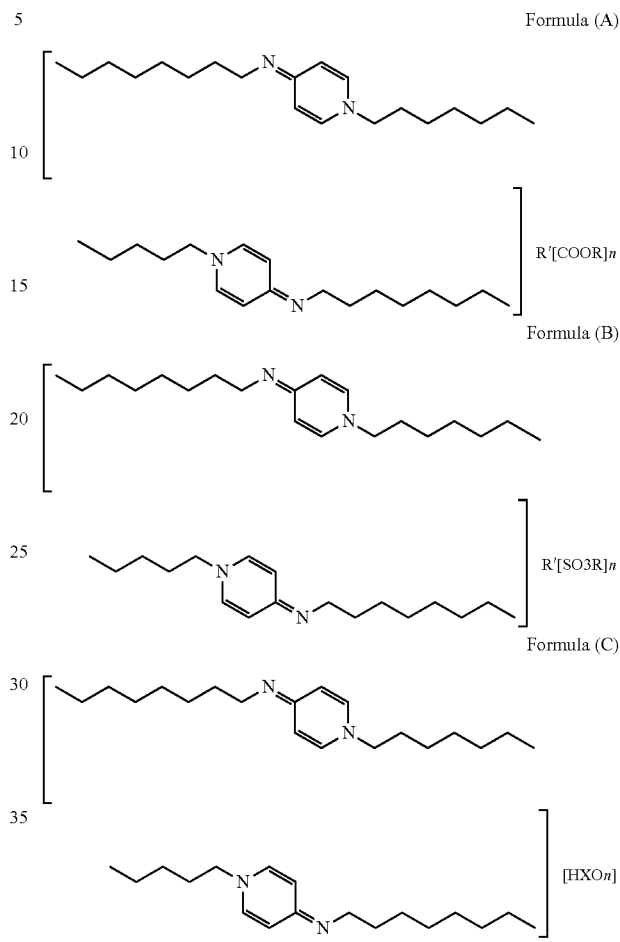

wherein, n=1, 2, 3, 4 and R'=un-substituted or substituted aryl or alkyl group; R is hydroxy or hydrogen; and X is chlorine, bromine or iodine.

2. A crystalline compound claimed in claim 1, wherein the unsubstituted or substituted aryl or alkyl group is selected from benzoic acid, salicylic acid, p-methyl benzoic acid, acetate, peracetic acid, oxalic acid, malonic acid, succinic acid, tartaric acid, and gluconate.

3. Octenidine benzoate in crystalline form having the formula A, B or C of claim 1, characterized characterised by an X-ray powder diffraction pattern with peaks at 4.75, 5.80, 6.30, 11.61, 12.59, 14.29, 15.10, 15.83, 17.64, 18.91, 19.39, 19.97, 21.16, 21.83, 22.40, 23.10, 23.54, 24.29, 25.39, 26.42, 27.12, 28.92, 30.40, 31.65, 32.89, 33.33, 35.88, 36.69, 38.03 and 39.58±0.2° 2θ; a differential scanning calorimetry (DSC) having endothermic peak at about 109.31° C. and 128.95° C.; Nuclear Magnetic Resonance pattern substantially as depicted in FIG. 2 and IR spectra substantially as depicted in FIG. 4.

4. Octenidine acetate in crystalline form having the formula A, B, or C of claim 1, characterized by X-ray powder diffraction pattern with peaks at 5.08, 7.68, 9.02, 10.02, 11.12, 12.30, 14.07, 14.92, 15.98, 17.02, 17.95, 19.77, 20.32, 20.83, 22.26, 22.77, 23.37, 24.14, 24.84, 25.52, 26.99, 27.32, 31.09, 32.43, 34.38 and 36.23±0.2° 2θ; a differential scanning calorimetry (DSC) having endothermic peak at about 203.56° C.; Nuclear Magnetic Resonance pattern substantially as depicted in FIG. 6 and IR spectra substantially as depicted in FIG. 8.

5. Octenidine gluconate in crystalline form having the formula A, B, or C of claim 1, characterized by X-ray powder diffraction pattern with peaks at 5.46, 10.70, 13.25, 14.89, 16.37, 19.32, 19.82, 20.58, 21.79, 23.26, 25.81, 26.32, 26.81, 30.00, 31.41, 32.09, 34.27, 35.56, 36.80, 38.11, 38.72 and 39.26±0.2° 2θ; a differential scanning calorimetry (DSC) having endothermic peak at about 87.46° C. and 206.97° C.; Nuclear Magnetic Resonance pattern substantially as depicted in FIG. 10 and IR spectra substantially as depicted in FIG. 12.

6. Octenidine peracetic acid in crystalline form having the formula A, B, or C of claim 1, characterized by X-ray powder diffraction pattern with peaks at 4.70, 6.32, 7.70, 8.51, 9.19, 10.15, 10.35, 11.45, 11.70, 12.74, 13.59, 14.07, 14.70, 15.37, 15.88, 16.25, 16.97, 17.28, 17.98, 18.99, 19.69, 19.99, 20.94, 22.53, 23.30, 23.62, 23.99, 24.74, 25.08, 25.99, 26.39, 26.87, 27.36, 28.16, 29.72, 31.68, 32.59, 33.05, 33.65, 35.54, 36.58, 37.14 and 37.57±0.2° 2θ; a differential scanning calorimetry (DSC) having endothermic peak at about 58.92° C. and 202.28° C.; Nuclear Magnetic Resonance pattern substantially as depicted in FIG. 14 and IR spectra substantially as depicted in FIG. 16.

7. Octenidine perchloric acid in crystalline form having the formula A, B, or C of claim 1, characterized by X-ray powder diffraction pattern with peaks at 5.25, 10.49, 12.80, 13.66, 14.54, 14.88, 15.18, 15.79, 16.87, 17.87, 18.35, 18.86, 19.18, 20.74, 21.50, 22.67, 23.09, 23.47, 25.34, 25.64, 26.60, 26.87, 28.99, 31.09, 31.68, 32.56, 34.87, 36.19, 36.86 and 39.10±0.2° 2θ; a differential scanning calorimetry (DSC) having endothermic peak at about 135.03° C.; Nuclear Magnetic Resonance pattern substantially as depicted in FIG. 18 and IR spectra substantially as depicted in FIG. 20.

8. Octenidine Lauric acid salt in crystalline form having the formula A, B, or C of claim 1, characterized characterised by X-ray powder diffraction pattern with peaks at 4.30, 5.92, 9.86, 10.06, 10.16, 10.74, 11.69, 12.63, 13.90, 15.60, 16.93, 17.74, 18.49, 19.11, 19.61, 20.06, 20.50, 21.00, 21.22, 21.68, 21.98, 22.83, 23.85, 23.99, 24.57, 24.98, 25.36, 26.25, 26.98, 27.53, 28.18, 29.02, 29.43, 30.15, 31.99, 35.39, 36.54, 37.50, 38.56 and 39.51±0.2° 2θ; a differential scanning calorimetry (DSC) having endothermic peak at about 137.63° C.; Nuclear Magnetic Resonance pattern substantially as depicted in FIG. 22 and IR spectra substantially as depicted in FIG. 24.

9. Octenidine palmitic acid in crystalline form having the formula A, B, or C of claim 1, characterized by X-ray powder diffraction pattern with peaks at 4.42, 5.03, 5.41, 5.84, 5.92, 6.59, 7.80, 9.72, 9.81, 10.11, 10.78, 10.95, 12.16, 13.62, 14.91, 15.60, 17.47, 19.05, 19.52, 20.12, 20.36, 20.48, 21.40, 22.22, 22.74, 23.82, 24.64, 25.74, 26.47, 27.41, 28.70, 30.11, 31.81, 33.76, 35.23, 37.20, 38.65 and 39.06±0.2° 2θ; a differential scanning calorimetry (DSC) having endothermic peak at about 77.58 and 102.74° C.; Nuclear Magnetic Resonance pattern substantially as depicted in FIG. 26 and IR spectra substantially as depicted in FIG. 28.

10. Octenidine methane sulfonic acid in crystalline form having the formula A, B, or C of claim 1, characterized by X-ray powder diffraction pattern with peaks at 4.74, 5.04, 5.32, 6.74, 8.10, 9.20, 10.18, 10.41, 11.16, 11.75, 13.17, 13.69, 14.16, 14.46, 15.01, 15.93, 17.01, 17.29, 18.08, 19.04, 19.26, 19.74, 19.99, 20.62, 21.37, 21.74, 22.29, 22.72, 23.34, 24.14, 24.32, 24.76, 25.39, 26.51, 26.95, 27.61, 28.29, 29.04, 29.66, 30.30, 30.95, 31.45, 31.93, 32.21, 33.17, 35.51, 37.53, 38.28 and 39.79±0.2° 2θ; a differential scanning calorimetry (DSC) having endothermic peak at about 102.45° C.; Nuclear Magnetic Resonance pattern substantially as depicted in FIG. 30 and IR spectra substantially as depicted in FIG. 32.

11. A process of preparation of crystalline Octenidine based compounds of formula (A) of claim 1, which comprises steps of:
(a) treating with Octenidine with suitable organic acid in a solvent;
(b) isolating the product as a salt with organic acid from an organic solvent;
(c) optionally purifying the salt from organic solvent.

12. The process as claimed in claim 11, wherein the organic acid is selected benzoic acid, salicylic acid, p-methyl benzoic acid, acetic acid, oxalic acid, malonic acid, succinic acid, tartaric acid, gluconic acid, lauric acid, and palmitic acid.

13. A process of preparation of crystalline Octenidine based compounds of formula (B) of claim 1, which comprises steps of:
(a) treating with Octenidine with sulfonic acid in a solvent;
(b) isolating the product as a salt with organic acid from an organic solvent;
(c) optionally purifying the salt from organic solvent.

14. The process as claimed in claim 13, wherein the sulfonic acid is selected from methane sulfonic acid, ethane sulfonic acid, propane sulfonic acid, benzene sulfonic acid, and p toluene sulfonic acid.

15. A process of preparation of crystalline Octenidine based compounds of formula (C) of claim 1, which comprises steps of:
(a) treating with Octenidine with per halogenate acid in a solvent;
(b) isolating the product as a salt with organic acid from an organic solvent;
(c) purifying the salt from organic solvent.

16. The process of claim 15 wherein the per halogenate acid is selected from HClO, $HClO_2$, $HClO_3$, $HClO_4$, HBrO, $HBrO_3$, $HBrO_4$, HIO, $HIO_3$, and $HIO_4$.

17. The process as claimed in claim 11, wherein the solvent is selected from branched or linear C1-C4 alcohols, ketones, esters, nitriles or halogenated solvents or aromatic hydrocarbons; and
wherein the linear alcohol (C1-C4) is selected from methanol, ethanol, isopropanol, n-propanol, n-butanol, iso-butanol, or tert-butanol;
wherein the ester is selected from ethyl acetate, isopropyl acetate, butyl acetate, iso-butyl acetate;
wherein the ketone is selected from acetone, methyl ethyl ketone, methyl tert-butyl ketone; and
wherein the ether is selected from tetrahydrofuran, diethyl ether, di isopropyl ether.

18. The process as claimed in claim 17, wherein the solvent is selected from dioxane; acetonitrile; ethylene dichloride, methylene dichloride; toluene, xylene, and hexane.

19. The process as claimed in claim 13, wherein the solvent is selected from branched or linear C1-C4 alcohols, ketones, esters, nitriles or halogenated solvents or aromatic hydrocarbons; and
wherein the linear alcohol (C1-C4) is selected from methanol, ethanol, isopropanol, n-propanol, n-butanol, iso-butanol, or tert-butanol;

wherein the ester is selected from ethyl acetate, isopropyl acetate, butyl acetate, iso-butyl acetate;

wherein the ketone is selected from acetone, methyl ethyl ketone, methyl tert-butyl ketone; and wherein the ether is selected from tetrahydrofuran, diethyl ether, di isopropyl ether.

20. The process as claimed in claim 15, wherein the solvent is selected from branched or linear C1-C4 alcohols, ketones, esters, nitriles or halogenated solvents or aromatic hydrocarbons; and wherein the linear alcohol (C1-C4) is selected from methanol, ethanol, isopropanol, n-propanol, n-butanol, iso-butanol, or tert-butanol;

wherein the ester is selected from ethyl acetate, isopropyl acetate, butyl acetate, iso-butyl acetate;

wherein the ketone is selected from acetone, methyl ethyl ketone, methyl tert-butyl ketone; and wherein the ether is selected from tetrahydrofuran, diethyl ether, di isopropyl ether.

* * * * *

UNITED STATES PATENT AND TRADEMARK OFFICE
CERTIFICATE OF CORRECTION

PATENT NO. : 11,014,907 B2
APPLICATION NO. : 16/640418
DATED : May 25, 2021
INVENTOR(S) : Janmejay Rajnikant Vyas and Nilesh Patel It is certified that error appears in the above-identified patent and that said Letters Patent is hereby corrected as shown below:

In the Claims

Column 18, Line 51, delete "characterised by" and insert --by--

Column 19, Lines 38 and 39, delete "characterised by" and insert --by--

Signed and Sealed this
Seventeenth Day of August, 2021

Drew Hirshfeld
*Performing the Functions and Duties of the*
*Under Secretary of Commerce for Intellectual Property and*
*Director of the United States Patent and Trademark Office*